US007312247B2

(12) United States Patent
Lan-Hargest et al.

(10) Patent No.: US 7,312,247 B2
(45) Date of Patent: Dec. 25, 2007

(54) HISTONE DEACETYLASE INHIBITORS

(75) Inventors: Hsuan-Yin Lan-Hargest, Fallston, MD (US); Robert J. Kaufman, St. Louis, MO (US); Norbert L Wiech, Phoenix, MD (US)

(73) Assignee: Errant Gene Therapeutics, LLC, Chicago, IL (US)

( * ) Notice: Subject to any disclaimer, the term of this patent is extended or adjusted under 35 U.S.C. 154(b) by 888 days.

(21) Appl. No.: 09/812,945

(22) Filed: Mar. 27, 2001

(65) Prior Publication Data

US 2002/0143052 A1    Oct. 3, 2002

(51) Int. Cl.
A61K 31/19    (2006.01)
(52) U.S. Cl. ...................................... 514/575
(58) Field of Classification Search ................. 514/575
See application file for complete search history.

(56) References Cited

U.S. PATENT DOCUMENTS

| | | | |
|---|---|---|---|
| 2,680,755 A | 6/1954 | Robeson et al. |
| 2,840,586 A | 6/1958 | Inhoffen |
| 3,479,396 A | 11/1969 | Buu-Hoi et al. |
| 3,551,574 A | 12/1970 | Frohberger et al. |
| 3,624,127 A | 11/1971 | Shaw et al. |
| 3,674,884 A | 7/1972 | Moritani et al. |
| 3,687,955 A | 8/1972 | Cerbati et al. |
| 3,755,604 A | 8/1973 | Gallo |
| 3,781,314 A | 12/1973 | Bollag et al. |
| 3,886,278 A | 5/1975 | Gallo |
| 3,909,353 A | 9/1975 | Tsuchida et al. |
| 3,978,100 A | 8/1976 | Fujita et al. |
| 3,984,440 A | 10/1976 | Bollag et al. |
| 4,011,339 A | 3/1977 | Galantay et al. |
| 4,024,182 A | 5/1977 | Kathawala |
| 4,044,149 A | 8/1977 | Fields et al. |
| 4,048,332 A | 9/1977 | Adams et al. |
| 4,061,656 A | 12/1977 | Klaus et al. |
| 4,081,476 A | 3/1978 | Anderson et al. |
| 4,113,858 A | 9/1978 | Hashim |
| 4,116,975 A | 9/1978 | Klaus et al. |
| 4,127,722 A | 11/1978 | Lafon |
| 4,127,723 A | 11/1978 | Yankee |
| 4,130,653 A | 12/1978 | Giroux et al. |
| 4,171,318 A | 10/1979 | Chan et al. |
| 4,188,338 A | 2/1980 | Bruins et al. |
| 4,193,931 A | 3/1980 | Loeliger |
| 4,211,783 A | 7/1980 | Shepherd |
| 4,258,057 A | 3/1981 | Bartmann et al. |
| 4,288,253 A | 9/1981 | Venable |
| 4,309,357 A | 1/1982 | Chiusoli et al. |
| 4,309,407 A | 1/1982 | Lautenschläger et al. |
| 4,335,054 A | 6/1982 | Blaser et al. |
| 4,355,168 A | 10/1982 | Chiusoli et al. |
| 4,371,614 A | 2/1983 | Anderson et al. |
| 4,388,459 A | 6/1983 | Shepherd |
| 4,439,443 A | 3/1984 | Giroux |
| 4,440,940 A | 4/1984 | Shepherd |
| 4,472,430 A | 9/1984 | Loev et al. |
| 4,504,494 A | 3/1985 | Grollier et al. |
| 4,505,930 A | 3/1985 | Loev et al. |
| 4,534,979 A | 8/1985 | Loev et al. |
| 4,545,984 A | 10/1985 | Möller et al. |
| 4,564,476 A | 1/1986 | Ho |
| 4,604,407 A | 8/1986 | Haslanger et al. |
| 4,605,669 A | 8/1986 | Summers, Jr. |
| 4,607,053 A | 8/1986 | Karanewsky et al. |
| 4,608,390 A | 8/1986 | Summers, Jr. |
| 4,619,945 A | 10/1986 | Loev et al. |
| 4,621,099 A | 11/1986 | Loev et al. |
| 4,623,661 A | 11/1986 | Summers, Jr. |
| 4,638,011 A | 1/1987 | Das |
| 4,699,920 A | 10/1987 | Skuballa et al. |
| 4,709,076 A | 11/1987 | Bombardelli et al. |
| 4,722,939 A | 2/1988 | Loev et al. |
| 4,731,382 A | 3/1988 | Zusi et al. |
| 4,753,934 A | 6/1988 | Nickl et al. |
| 4,791,133 A | 12/1988 | Djuric et al. |
| 4,820,828 A | 4/1989 | Demers et al. |
| 4,833,257 A | 5/1989 | Pettit et al. |
| 4,950,467 A | 8/1990 | Phalangas et al. |

(Continued)

FOREIGN PATENT DOCUMENTS

| EP | 0 161 939 | 11/1985 |
|---|---|---|
| EP | 0 199 151 | 10/1986 |
| WO | WO98/55449 | * 12/1998 |
| WO | WO 01/18171 | 3/2001 |
| WO | WO 01/38322 | 5/2001 |

OTHER PUBLICATIONS

Richon et al., A class of hybrid polar inducers of transformed cell differentiation inhibits histone descetylase, abstract, Mar. 1998.*
Marks et al., "Histone Daecetylase Inhibitors", J. of Natl. Cancer Inst., vol. 92 No. 15 1210-1216 (2000).*
Richon et al. 'A class of hybrid polar inducers of transformed cell diferentiation inhibits histone deacetylases,' Proc. Natl. Acad. Sci. USA 1998, vol. 95, pp. 3003-3007.*
Andrews et al., "Anti-malarial effect of histone deacetylation inhibitors and mammalian tumour cytodifferentiating agents", International Journal for Parasitology, 30, pp. 761-768, (2000).

(Continued)

Primary Examiner—Shengjun Wang
(74) Attorney, Agent, or Firm—Steptoe & Johnson LLP

(57) ABSTRACT

Histone deacetylase is a metallo-enzyme with zinc at the active site. Compounds having a zinc-binding moiety, such as, for example, a hydroxamic acid group or a carboxylic acid group, can inhibit histone deacetylase. Histone deacetylase inhibition can repress gene expression, including expression of genes related to tumor suppression. Accordingly, inhibition of histone deacetylase can provide an alternate route for treating cancer, hematological disorders, e.g., hemoglobinopathies, and genetic related metabolic disorders, e.g., cystic fibrosis and adrenoleukodystrophy.

11 Claims, No Drawings

U.S. PATENT DOCUMENTS

| | | | |
|---|---|---|---|
| 4,981,865 | A | 1/1991 | Belliotti et al. |
| 4,985,436 | A | 1/1991 | Pettit |
| 5,028,629 | A | 7/1991 | Hite et al. |
| 5,064,860 | A | 11/1991 | Mueller et al. |
| 5,075,330 | A | 12/1991 | Belliotti et al. |
| 5,084,214 | A | 1/1992 | Kita et al. |
| 5,089,524 | A | 2/1992 | Collins et al. |
| 5,091,569 | A | 2/1992 | Matsumoto et al. |
| 5,112,846 | A | 5/1992 | Belliotti et al. |
| 5,141,959 | A | 8/1992 | Carroll et al. |
| 5,235,068 | A | 8/1993 | Minai et al. |
| 5,244,922 | A | 9/1993 | Burzynski |
| 5,246,955 | A | 9/1993 | Skibo et al. |
| 5,264,424 | A | 11/1993 | Della Valle et al. |
| 5,272,180 | A | 12/1993 | Hashimoto et al. |
| 5,320,833 | A | 6/1994 | Deckers et al. |
| 5,369,108 | A | 11/1994 | Breslow et al. |
| 5,385,942 | A | 1/1995 | Abe et al. |
| 5,420,160 | A | 5/1995 | Gayer et al. |
| 5,466,718 | A | 11/1995 | Nakatsu et al. |
| 5,475,022 | A | 12/1995 | Chandraratna |
| 5,486,540 | A | 1/1996 | Andrews |
| 5,525,629 | A | 6/1996 | Crimmin et al. |
| 5,541,155 | A | 7/1996 | Leone-Bay et al. |
| 5,547,988 | A | 8/1996 | Yu et al. |
| 5,602,135 | A | 2/1997 | Chandraratna |
| 5,607,978 | A | 3/1997 | Woodward et al. |
| 5,643,949 | A | 7/1997 | Van Scott et al. |
| 5,672,746 | A | 9/1997 | Nau et al. |
| 5,677,320 | A | 10/1997 | Chandraratna |
| 5,688,819 | A | 11/1997 | Woodward et al. |
| 5,696,162 | A | 12/1997 | Chandraratna |
| 5,705,167 | A | 1/1998 | Bernardon et al. |
| 5,710,178 | A | 1/1998 | Samid |
| 5,872,152 | A | 2/1999 | Brown et al. ............... 523/115 |
| 6,057,369 | A | 5/2000 | Groneberg et al. ......... 514/575 |
| 6,451,334 | B2 | 9/2002 | Perrine ...................... 424/423 |
| RE37,947 | E | 12/2002 | Bernardon et al. ......... 424/401 |
| 6,511,990 | B1 * | 1/2003 | Breslow et al. ............. 514/314 |

OTHER PUBLICATIONS

Collins et al., "Oral Sodium Phenylbutyrate Therapy in Homozygous β Thalassemia: A Clinical Trial", Blood, vol. 85, No. 1, pp. 43-49, (1995).

Finnin et al., "Structures of a histone deacetylase homologue bound to the TSA and SAHA inhibitors", Nature, vol. 401, pp. 188-193, (1999).

Fruehauf et al., "In Vitro Determination of Drug Response: A Discussion of Clinical Applications", Principles & Practice of Oncology, vol. 7 No. 12, pp. 1-16, (1993).

Gore et al., "Modifying histones to tame cancer: clinical development of sodium phenylbutyrate and other histone deacetylase inhibitors", Exp. Opin. Invest. Drugs, 9(12), pp. 2923-2934, (2000).

Hoffman et al., "A non-isotopic assay for histone deacetylase activity", Nucleic Acids Research, vol. 27, No. 9, pp. 2057-2058, (1999).

Kemp et al., "Gene redundancy and pharmacological gene therapy: Implications for X-linked adrenoleukodystrophy", Nature Medicine, vol. 4, No. 11, pp. 1261-1268, (1998).

Kim et al., "Oxamflatin is a novel antitumor compound that inhibits mammalian histone deacetylase", Oncogene, vol. 18, pp. 2461-2470, (1999).

Marks et al., "Histone Deacetylase Inhibitors: Inducers of Differentiation or Apoptosis of Transformed Cells", Journal of the National Cancer Institute, vol. 92, No. 15, pp. 1210-1216, (2000).

Remiszewski et al., "Synthesis and in Vitro SAR of Straight Chain Hydroxamate Histone Deacetylase Inhibitors", Proceedings of the AACR, vol. 42, No. 4976, (Feb. 27, 2001).

Rubenstein et al., "In Vitro Pharmacologic Restoration of CFTR-mediated Chloride Transport with Sodium 4-Phenylbutyrate in Cystic Fibrosis Epithelial Cells Containing ΔF508-CFTR", J. Clin. Invest., vol. 100, No. 10, pp. 2457-2465, (1997).

Sandler et al., "Organic Functional Group Preparations", Academic Press, New York and London, vol. III, pp. 436-437, (1972).

Saunders et al., Histone deacetylase inhibitors: novel anticancer agents, Exp. Opin. Invest. Drugs, 8(10), pp. 1611-1621, (1999).

Taunton et al., "A Mammalian Histone Deacetylase Related to the Yeast Transcriptional Regulator Rpd3p", Science, vol. 272, pp. 408-411, (1996).

Summers et al. "Hydroxamic Acid Inhibitors of 5-Lipoxygenase: Quantitative Structure-Activity Relationships," *Journal of Medical Chemistry*, vol. 33, pp. 992-998 (1990).

Egan et al. "Modulation of Ion Transport in Cultured Rabbit Tracheal Epithelium by Lipoxygenase," *American Journal of Respiratory Cell and Molecular Biology*, vol. 7, pp. 500-506 (1992).

\* cited by examiner

HISTONE DEACETYLASE INHIBITORS

TECHNICAL FIELD

This invention relates to enzyme inhibitors, and more particularly to histone deacetylase inhibitors.

BACKGROUND

DNA in the nucleus of the cell exists as a hierarchy of compacted chromatin structures. The basic repeating unit in chromatin is the nucleosome. The nucleosome consists of a histone octomer of proteins in the nucleus of the cell around which DNA is twice wrapped. The orderly packaging of DNA in the nucleus plays an important role in the functional aspects of gene regulation. Covalent modifications of the histones have a key role in altering chromatin higher order structure and function and ultimately gene expression. The covalent modification of histones occurs by enzymatically mediated processes, such as acetylation.

Regulation of gene expression through the inhibition of the nuclear enzyme histone deacetylase (HDAC) is one of several possible regulatory mechanisms whereby chromatin activity can be affected. The dynamic homeostasis of the nuclear acetylation of histones can be regulated by the opposing activity of the enzymes histone acetyl transferase (HAT) and histone deacetylase (HDAC). Transcriptionally silent chromatin can be characterized by nucleosomes with low levels of acetylated histones. Acetylation of histones reduces its positive charge, thereby expanding the structure of the nucleosome and facilitating the interaction of transcription factors to the DNA. Removal the acetyl group restores the positive charge condensing the structure of the nucleosome. Acetylation of histone-DNA activates transcription of DNA's message, an enhancement of gene expression. Histone deacetylase can reverse the process and can serve to repress gene expression. See, for example, Grunstein, *Nature* 389, 349–352 (1997); Pazin et al., *Cell* 89, 325–328 (1997); Wade et al., *Trends Biochem. Sci.* 22, 128–132 (1997); and Wolffe, *Science* 272, 371–372 (1996).

SUMMARY

Histone deacetylase is a metallo-enzyme with zinc at the active site. Compounds having a zinc-binding moiety, such as, for example, a hydroxamic acid group or a carboxylic acid group, can inhibit histone deacetylase. Histone deacetylase inhibition can repress gene expression, including expression of genes related to tumor suppression. Accordingly, inhibition of histone deacetylase can provide an alternate route for treating cancer, hematological disorders, e.g., hemoglobinopathies, and genetic related metabolic disorders, e.g., cystic fibrosis and adrenoleukodystrophy.

In one aspect, a method of inhibiting histone deacetylation activity in cells includes contacting the cells with an effective amount of a compound of formula (I), thereby treating one or more disorders mediated by histone deacetylase, and determining whether the level of acetylated histones in the treated cells is higher than in untreated cells under the same conditions.

The compound of formula (I) can be the following:

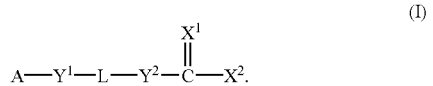

(I)

A is a cyclic moiety selected from the group consisting of $C_{3-14}$ cycloalkyl, 3–14 membered heterocycloalkyl, $C_{4-14}$ cycloalkenyl, 4–14 membered heterocycloalkenyl, aryl, or heteroaryl; the cyclic moiety being optionally substituted with alkyl, alkenyl, alkynyl, alkoxy, hydroxyl, hydroxylalkyl, halo, haloalkyl, amino, alkylcarbonyloxy, alkyloxycarbonyl, alkylcarbonyl, alkylsulfonylamino, aminosulfonyl, or alkylsulfonyl; or A is a saturated branched $C_{3-12}$ hydrocarbon chain or an unsaturated branched $C_{3-12}$ hydrocarbon chain optionally interrupted by —O—, —S—, —N($R^a$)—, —C(O)—, —N($R^a$)—SO$_2$—, —SO$_2$—N($R^a$)—, —N($R^a$)—C(O)—O—, —O—C(O)—N($R^a$)—, —N($R^a$)—C(O)—N($R^b$)—, —O—C(O)—, —C(O)—O—, —O—SO$_2$—, —SO$_2$—O—, or —O—C(O)—O—, where each of $R^a$ and $R^b$, independently, is hydrogen, alkyl, alkenyl, alkynyl, alkoxy, hydroxylalkyl, hydroxyl, or haloalkyl; each of the saturated and the unsaturated branched hydrocarbon chain being optionally substituted with alkyl, alkenyl, alkynyl, alkoxy, hydroxyl, hydroxylalkyl, halo, haloalkyl, amino, alkylcarbonyloxy, alkyloxycarbonyl, alkylcarbonyl, alkylsulfonylamino, aminosulfonyl, or alkylsulfonyl. Each of $Y^1$ and $Y^2$, independently, is —CH$_2$—, —O—, —S—, —N($R^c$)—, —N($R^c$)—C(O)—O—, —O—C(O)—N($R^c$)—, —N($R^c$)—C(O)—N($R^d$)—, —O—C(O)—O—, or a bond, and each of $R^c$ and $R^d$, independently, being hydrogen, alkyl, alkenyl, alkynyl, alkoxy, hydroxylalkyl, hydroxyl, or haloalkyl. L is a straight $C_{2-12}$ hydrocarbon chain optionally containing at least one double bond, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, amino, nitro, cyano, $C_{3-5}$ cycloalkyl, 3–5 membered heterocycloalkyl, monocyclic aryl, 5–6 membered heteroaryl, $C_{1-4}$ alkylcarbonyloxy, $C_{1-4}$ alkyloxycarbonyl, $C_{1-4}$ alkylcarbonyl, or formyl; and further being optionally interrupted by —O—, —N($R^e$)—, —N($R^e$)—C(O)—O—, —O—C(O)—N($R^e$)—, —N($R^e$)—C(O)—N($R^f$)—, or —O—C(O)—O—; each of $R^e$ and $R^f$, independently, being hydrogen, alkyl, alkenyl, alkynyl, alkoxy, hydroxylalkyl, hydroxyl, or haloalkyl. $X^1$ is O or S. $X^2$ is —O$R^1$, —S$R^1$, —N$R^3$—O$R^1$, —N$R^3$—S$R^1$, —C(O)—O$R^1$, —CH$R^4$—O$R^1$, —N=N—C(O)—N($R^3$)$_2$, or —O—CH$R^4$—O—C(O)—$R^5$, where each of $R^1$ and $R^2$, independently, is hydrogen, alkyl, hydroxylalkyl, haloalkyl, or a hydroxyl protecting group, $R^3$ is hydrogen, alkyl, alkenyl, alkynyl, alkoxy, hydroxylalkyl, hydroxyl, haloalkyl, or an amino protecting group, $R^4$ is hydrogen, alkyl, hydroxylalkyl, or haloalkyl, and $R^5$ is alkyl, hydroxylalkyl, or haloalkyl. When L is a $C_{2-3}$ hydrocarbon containing no double bonds and $X^2$ is —O$R^1$, $Y^1$ is not a bond and $Y^2$ is not a bond.

In another aspect, a method of inhibiting histone deacetylase in cells comprising contacting the cells with an effective amount of a compound of formula (I), supra, and determining whether the level of acetylated histones in the treated cells is higher than in untreated cells under the same conditions. A is phenyl optionally substituted with alkyl alkenyl, alkynyl, alkoxy, hydroxyl, hydroxylalkyl, halo, haloalkyl, or amino. Each of $Y^1$ and $Y^2$, independently, is —CH$_2$—, —O—, —S—, —N($R^c$)—, or a bond; where RC is hydrogen, alkyl, alkenyl, alkynyl, alkoxy, hydroxylalkyl, hydroxyl, or haloalkyl. L is a straight $C_{2-12}$ hydrocarbon chain optionally containing at least one double bond, at least one triple bond, or at least one double bond and one triple bond, the hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, amino, nitro, cyano, $C_{3-5}$ cycloalkyl, 3–5 membered heterocycloalkyl, monocyclic aryl, 5–6 membered heteroaryl, $C_{1-4}$ alkylcarbonyloxy., $C_{1-4}$ alkyloxycarbonyl, $C_{1-4}$ alkylcarbonyl, or formyl; and further being optionally interrupted by —O—, —N($R^e$)—, —N($R^e$)—C(O)—O—, —O—C(O)—N($R^e$)—, —N($R^e$)—C(O)—N($R^f$)—, or —O—C(O)—O—, and each of $R^e$ and $R^f$, independently, being hydrogen, alkyl, alkenyl, alkynyl, alkoxy, hydroxylalkyl, hydroxyl, or haloalkyl. $X^1$ is O or S. $X^2$ is —$OR^1$, —$SR^1$, —$NR^3$—$OR^1$, —$NR^3$—$SR^1$, —C(O)—$OR^1$, —$CHR^4$—$OR^1$, —N=N—C(O)—N($R^3$)$_2$, or —O—$CHR^4$—O—C(O)—$R^5$, where each of $R^1$ and $R^2$, independently, is hydrogen, alkyl, hydroxylalkyl, haloalkyl, or a hydroxyl protecting group, $R^3$ is hydrogen, alkyl, alkenyl, alkynyl, alkoxy, hydroxylalkyl, hydroxyl, haloalkyl, or an amino protecting group, $R^4$ is hydrogen, alkyl, hydroxylalkyl, or haloalkyl, and $R^5$ is alkyl, hydroxylalkyl, or haloalkyl. When L is a $C_{2-3}$ hydrocarbon containing no double bonds and $X^2$ is —$OR^1$, $Y^1$ is not a bond and $Y^2$ is not a bond.

In yet another aspect, a method of treating a histone deacetylase-mediated disorder includes administering to a subject in need thereof a therapeutically effective amount of compound of formula (I), supra.

In certain embodiments, $X^2$ can be —$OR^1$, —$NR^3$—$OR^1$, —C(O)—$OR^1$, —$CHR^4$—$OR^1$, or —O—$CHR^4$—O—C(O)—$R^5$, $X^2$ can be —$OR^1$, —$NR^3$—OR, —C(O)$OR^1$, or —O—$CHR^4$—O—C(O)—$R^5$, each of $Y^1$ and $Y^2$, independently, can be —$CH_2$—, —O—, —N($R^c$)—, or a bond, L can be a saturated hydrocarbon chain, such as a $C_{3-8}$ hydrocarbon chain substituted with $C_{1-2}$ alkyl, $C_{1-2}$ alkoxy, hydroxyl, —$NH_2$, —NH($C_{1-2}$ alkyl), or —N($C_{1-2}$ alkyl)$_2$.

In other embodiments, L can be an unsaturated hydrocarbon chain containing at least one double bond and no triple bond, such as an unsaturated $C_{4-8}$ hydrocarbon chain substituted with $C_{1-2}$ alkyl, $C_{1-2}$ alkoxy, hydroxyl, —$NH_2$, —NH($C_{1-2}$ alkyl), or —N($C_{1-2}$ alkyl)$_2$. In other embodiments, L can be an unsaturated hydrocarbon chain containing at least one double bond and one triple bond, such as an unsaturated $C_{48}$ hydrocarbon chain substituted with $C_{1-2}$ alkyl, $C_{1-2}$ alkoxy, hydroxyl, —$NH_2$, —NH($C_{1-2}$ alkyl), or —N($C_{1-2}$ alkyl)$_2$. The double bond can be in trans configuration.

In certain embodiments, A can be a $C_{5-8}$ cycloalkenyl or 5–8 membered heteroalkenyl containing at least one double bond. A can be phenyl, naphthyl, indanyl, or tetrahydronaphthyl, or A can be phenyl optionally substituted with alkyl alkenyl, alkynyl, alkoxy, hydroxyl, hydroxylalkyl, halo, haloalkyl, or amino. In other embodiments, A can contain only double bonds.

Set forth below are some examples of a compound that can be employed in the methods of the present invention: 5-phenyl-2,4-pentadienoic acid, 3-methyl-5-phenyl-2,4-pentadienoic acid, 4-methyl-5-phenyl-2,4-pentadienoic acid, 4-chloro-5-phenyl-2,4-pentadienoic acid, 5-(4-dimethylaminophenyl)-2,4-pentadienoic acid, 5-(2-furyl)-2,4-pentadienoic acid, 5-phenyl-2-en-4-yn-pentanoic acid, 6-phenyl-3,5-hexadienoic acid, 7-phenyl-2,4,6-heptatrienoic acid, 8-phenyl-3,5,7-octatrienoic acid, potassium 2-oxo-6-phenyl-3,5-hexadienoate, potassium 2-oxo-8-phenyl-3,5,7-octatrienoate, cinnamoylhydroxamic acid, methylcinnamoylhydroxamic acid, 4-cyclohexanebutyroylhydroxamic acid, benzylthioglycoloylhydroxamic acid, 5-phenylpentanoylhydroxamic acid, 5-phenyl-2,4-pentadienoylhydroxamic acid, N-methyl-5-phenyl-2,4-pentadienoylhydroxamic acid, 3-methyl-5-phenyl-2,4-pentadienoylhydroxamic acid, 4-methyl-5-phenyl-2,4-pentadienoylhydroxamic acid, 4-chloro-5-phenyl-2,4-pentadienoylhydroxamic acid, 5-(4-dimethylaminophenyl)-2,4-pentadienoylhydroxamic acid, 5-phenyl-2-en-4-yn-pentanoylhydroxamic acid, 5-(2-furyl)-2,4-pentadienoylhydroxamic acid, 6-phenylhexanoylhydroxamic acid, 6-phenyl-3,5-hexadienoylhydroxamic acid, N-methyl-6-phenyl-3,5-hexadienoylhydroxamic acid, 7-phenylheptanoylhydroxamic acid, 7-phenyl-2,4,6-hepta-trienoylhydroxamic acid or 8-phenyloctanoylhydroxamic acid.

A salt of any of the compounds of the invention can be prepared. For example, a pharmaceutically acceptable salt can be formed when an amino-containing compound of this invention reacts with an inorganic or organic acid. Some examples of such an acid include hydrochloric acid, hydrobromic acid, hydroiodic acid, sulfuric acid, phosphoric acid, p-bromophenylsulfonic acid, carbonic acid, succinic acid, citric acid, benzoic acid, and acetic acid. Examples of pharmaceutically acceptable salts thus formed include sulfate, pyrosulfate bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, and maleate. A compound of this invention may also form a pharmaceutically acceptable salt when a compound of this invention having an acid moiety reacts with an inorganic or organic base. Such salts include those derived from inorganic or organic bases, e.g., alkali metal salts such as sodium, potassium, or lithium salts; alkaline earth metal salts such as calcium or magnesium salts; or ammonium salts or salts of organic bases such as morpholine, piperidine, pyridine, dimethylamine, or diethylamine salts.

It should be recognized that a compound of the invention can contain chiral carbon atoms. In other words, it may have optical isomers or diastereoisomers.

Alkyl is a straight or branched hydrocarbon chain containing 1 to 10 (preferably, 1 to 6; more preferably 1 to 4) carbon atoms. Examples of alkyl include, but are not limited to, methyl, ethyl, propyl, isopropyl, butyl, isobutyl, sec-butyl, tert-butyl, n-pentyl, 2-methylhexyl, and 3-ethyloctyl.

The terms "alkenyl" and "alkynyl" refer to a straight or branched hydrocarbon chain containing 2 to 10 carbon atoms and one or more (preferably, 1–4 or more preferably 1–2) double or triple bonds, respectively. Some examples of alkenyl and alkynyl are allyl, 2-butenyl, 2-pentenyl, 2-hexenyl, 2-butynyl, 2-pentynyl, and 2-hexynyl.

Cycloalkyl is a monocyclic, bicyclic or tricyclic alkyl group containing 3 to 14 carbon atoms. Some examples of cycloalkyl are cyclopropyl, cyclopentyl, cyclohexyl, cycloheptyl, adamantyl, and norbornyl. Heterocycloalkyl is a cycloalkyl group containing at least one heteroatom (e.g., 1–3) such as nitrogen, oxygen, or sulfur. The nitrogen or sulfur may optionally be oxidized and the nitrogen may optionally be quaternized. Examples of heterocycloalkyl include piperidinyl, piperazinyl, tetrahydropyranyl, tetrahydrofuryl, and morpholinyl. Cycloalkenyl is a cycloalkyl group containing at least one (e.g., 1–3) double bond. Examples of such a group include cyclopentenyl, 1,4-cyclohexa-di-enyl, cycloheptenyl, and cyclooctenyl groups. By the same token, heterocycloalkenyl is a cycloalkenyl group containing at least one heteroatom selected from the group of oxygen, nitrogen or sulfur.

Aryl is an aromatic group containing a 5–14 ring and can contain fused rings, which may be saturated, unsaturated, or aromatic. Examples of an aryl group include phenyl, naphthyl, biphenyl, phenanthryl, and anthracyl. If the aryl is specified as "monocyclic aryl," if refers to an aromatic group containing only a single ring, i.e., not a fused ring.

Heteroaryl is aryl containing at least one (e.g., 1–3) heteroatom such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

The cyclic moiety can be a fused ring formed from two or more of the just-mentioned groups. Examples of a cyclic moiety having fused rings include fluorenyl, dihydro-dibenzoazepine, dibenzocycloheptenyl, 7H-pyrazino[2,3-c]carbazole, or 9,10-dihydro-9,10-[2]buteno-anthracene.

Amino protecting groups and hydroxy protecting groups are well-known to those in the art. In general, the species of protecting group is not critical, provided that it is stable to the conditions of any subsequent reaction(s) on other positions of the compound and can be removed without adversely affecting the remainder of the molecule. In addition, a protecting group may be substituted for another after substantive synthetic transformations are complete. Examples of an amino protecting group include, but not limited to, carbamates such as 2,2,2-trichloroethylcarbamate or tertbutylcarbamate. Examples of a hydroxyl protecting group include, but not limited to, ethers such as methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloro-ethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other protecting groups and reaction conditions can be found in T. W. Greene, *Protective Groups in Organic Synthesis*, (3rd, 1999, John Wiley & Sons, New York, N.Y.).

Note that an amino group can be unsubstituted (i.e., —$NH_2$), mono-substituted (i.e., —NHR), or di-substituted (i.e., —$NR_2$). It can be substituted with groups (R) such as alkyl, cycloalkyl, heterocycloalkyl, aryl, heteroaryl, aralkyl, or heteroaralkyl. Halo refers to fluoro, chloro, bromo, or iodo.

Inhibition of a histone deacetylase in a cell is determined by measuring the level of acetylated histones in the treated cells and measuring the level of acetylated histones in untreated cells and comparing the levels. If the level of histone acetylation in the treated cells increases relative to the untreated cells, histone deacetylase has been inhibited.

Some disorders or physiological conditions may be mediated by hyperactive histone deacetylase activity. A disorder or physiological condition that is mediated by histone deacetylase refers to a disorder or condition wherein histone deacetylase plays a role in triggering the onset thereof. Examples of such disorders or conditions include, but not limited to, cancer, hemoglobinopathies (e.g., thalassemia or sickle cell anemia), cystic fibrosis, protozoan infection, adrenoleukodystrophy, alpha-1 anti-trypsin, retrovirus gene vector reactivation, wound healing, hair growth, peroxisome biogenesis disorder, and adrenoleukodystrophy.

Other features or advantages will be apparent from the following detailed description of several embodiments, and also from the appended claims.

DETAILED DESCRIPTION

A carboxylic acid-containing compound of the present invention can be prepared by any known methods in the art. For example, a compound of the invention having an unsaturated hydrocarbon chain between A and —C(=$X^1$)— can be prepared according to the following scheme:

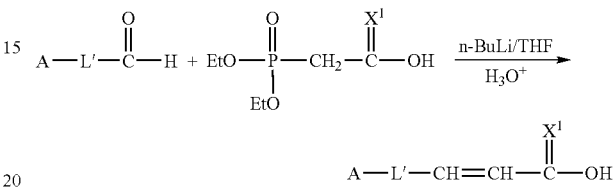

where L' is a saturated or unsaturated hydrocarbon linker between A and —CH=CH— in a compound of the invention, and A and $X^1$ has the same meaning as defined above. See Coutrot et al., *Syn. Comm.* 133–134 (1978). Briefly, butyllithium was added to an appropriate amount of anhydrous tetrahydrofuran (THF) at a very low temperature (e.g., −65° C.). A second solution having diethylphosphonoacetic acid in anhydrous THF was added dropwise to the stirred butyllithium solution at the same low temperature. The resulting solution is stirred at the same temperature for an additional 30–45 minutes which is followed by the addition of a solution containing an aromatic acrylaldehyde in anhydrous THF over 1–2 hours. The reaction mixture is then warmed to room temperature and stirred overnight. It is then acidified (e.g., with HCl) which allows the organic phase to be separated. The organic phase is then dried, concentrated, and purified (e.g., by recrystallization) to form an unsaturated carboxylic acid.

Alternatively, a carboxylic acid-containing compound can be prepared by reacting an acid ester of the formula A—L'—C(=O)—O-lower alkyl with a Grignard reagent (e.g., methyl magnesium iodide) and a phosphorus oxychloride to form a corresponding aldehyde, which can be further oxidized (e.g., by reacting with silver nitrate and aqueous NaOH) to form an unsaturated carboxylic acid.

Other types of carboxylic acid-containing compounds (e.g., those containing a linker with multiple double bonds or triple bonds) can be prepared according to published procedures such as those described, for example, in Parameswara et al., *Synthesis,* 815–818 (1980) and Denny et al., *J. Org. Chem.,* 27, 3404 (1962).

Carboxylic acid-containing compounds described above can then be converted to hydroxamic acid-containing compounds according to the following scheme:

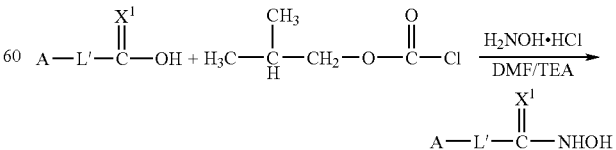

Triethylamine (TEA) is added to a cooled (e.g., 0–5° C.) anhydrous THF solution containing the carboxylic acid.

Isobutyl chloroformate is then added to the solution having carboxylic acid, which is followed by the addition of hydroxylamine hydrochloride and TEA. After acidification, the solution was filtered to collect the desired hydroxamic acid.

An N-substituted hydroxamic acid can be prepared in a similar manner as described above. A corresponding carboxylic acid A—L'—C(=O)—OH can be converted to an acid chloride by reacting with oxalyl chloride (in appropriate solvents such as methylene chloride and dimethylformamide), which in turn, can be converted to a desired N-substituted hydroxamic acid by reacting the acid chloride with an N-substituted hydroxylamine hydrochloride (e.g., $CH_3NHOH \cdot HCl$) in an alkaline medium (e.g., 40% NaOH (aq)) at a low temperature (e.g., 0–5° C.). The desired N-substituted hydroxamic acid can be collected after acidifying the reaction mixture after the reaction has completed (e.g., in 2–3 hours).

As to compounds of the invention wherein $X^1$ is S, they can be prepared according to procedures described in Sandler, S. R. and Karo, W., *Organic Functional Group Preparations, Volume III* (Academic Press, 1972) at pages 436–437. For preparation of compounds of the invention wherein $X^2$ is —N($R^c$)OH— and $X^1$ is S, see procedures described in U.S. Pat. Nos. 5,112,846; 5,075,330 and 4,981,865.

Compounds of the invention containing an α-keto acid moiety (e.g., when $X^1$ is oxygen and $X^2$ is —C(=O)OM or A—L'—C(=O)—C(=O)—OM, where A and L' have been defined above and M can be hydrogen, lower alkyl or a cation such as $K^+$), these compounds can be prepared by procedures based on that described in Schummer et al., *Tetrahedron*, 43, 9019 (1991). Briefly, the procedure starts with a corresponding aldehyde-containing compound (e.g., A—L'—C(=O)—H), which is allowed to react with a pyruvic acid in a basic condition (KOH/methanol) at a low temperature (e.g., 0–5° C.). Desired products (in the form of a potassium salt) are formed upon warming of the reaction mixture to room temperature.

The compounds described above, as well as their (thio) hydroxamic acid or α-keto acid counterparts, can possess histone deacetylase inhibitory properties.

Note that appropriate protecting groups may be needed to avoid forming side products during the preparation of a compound of the invention. For example, if the linker L' contains an amino substituent, it can be first protected by a suitable amino protecting group such as trifluoroacetyl or tert-butoxycarbonyl prior to being treated with reagents such as butyllithium. See, e.g., T. W. Greene, supra, for other suitable protecting groups.

A compound produced by the methods shown above can be purified by flash column chromatography, preparative high performance liquid chromatography, or crystallization.

A pharmaceutical composition can be used to inhibit histone deacetylase in cells and can be used to treat disorders associated with abnormal histone deacetylase activity. Some examples of these disorders are cancers (e.g., leukemia, lung cancer, colon cancer, CNS cancer, melanoma, ovarian cancer, cervical cancer, renal cancer, prostate cancer, and breast cancer), hematological disorders (e.g., hemoglobinopathies, thalassemia, and sickle cell anemia) and genetic related metabolic disorders (e.g., cystic fibrosis, peroxisome biogenesis disorder, alpha-1 anti-trypsin, and adrenoleukodystrophy). The compounds of this invention can also stimulate hematopoietic cells ex vivo, ameliorating protozoal parasitic infection, accelerate wound healing, and protecting hair follicles.

An effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.* 50, 219 (1966). Body surface area may be approximately determined from height and weight of the patient. See, e.g., *Scientific Tables*, Geigy Pharmaceuticals, Ardley, N.Y., 1970, 537. An effective amount of a compound described herein can range from about 1 mg/kg to about 300 mg/kg. Effective doses will also vary, as recognized by those skilled in the art, dependant on route of administration, excipient usage, and the possibility of co-usage, pre-treatment, or post-treatment, with other therapeutic treatments including use of other chemotherapeutic agents and radiation therapy. Other chemotherapeutic agents that can be co-administered (either simultaneously or sequentially) include, but not limited to, paclitaxel and its derivatives (e.g., taxotere), doxorubicin, L-asparaginase, dacarbazine, amascrine, procarbazine, hexamethylmelamine, mitoxantrone, and gemicitabine.

The pharmaceutical composition may be administered via the parenteral route, including orally, topically, subcutaneously, intraperitoneally, intramuscularly, and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds. Because some of the, compounds described herein can have limited water solubility, a solubilizing agent can be included in the composition to improve the solubility of the compound. For example, the compounds can be solubilized in polyethoxylated castor oil (Cremophor EL®) and may further contain other solvents, e.g., ethanol. Furthermore, compounds described herein can also be entrapped in liposomes that may contain tumor-directing agents (e.g., monoclonal antibodies having affinity towards tumor cells).

A compound described herein can be formulated into dosage forms for other routes of administration utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of a compound described herein with a solid carrier and a lubricant. Examples of solid carriers include starch and sugar bentonite. Compounds of this invention can also be administered in a form of a hard shell tablet or a capsule containing a binder, e.g., lactose or mannitol, a conventional filler, and a tableting agent.

The activities of a compound described herein can be evaluated by methods known in the art, e.g., MTT (3-[4,5-dimehtythiazol-2-yl]3-2,5-diphenyltetrazolium bromide) assay, clonogenic assay, ATP assay, or Extreme Drug Resistance (EDR) assay. See Freuhauf, J. P. and Manetta, A., *Chemosensitivity Testing in Gynecologic Malignancies and Breast Cancer* 19, 39–52 (1994). The EDR assay, in particular, is useful for evaluating the antitumor and antiproliferative activity of a compound of this invention (see Example 28 below). Cells are treated for four days with compound of the invention. Both untreated and treated cells are pulsed with tritiated thymidine for 24 hours. Radioactivity of each type of cells is then measured and compared.

The results are then plotted to generate drug response curves, which allow $IC_{50}$ values (the concentration of a compound required to inhibit 50% of the population of the treated cells) to be determined.

The histone acetylation activity of a compound described herein can be evaluated in an assay using mouse erythroleukemia cells. Studies are performed with the DS 19 mouse erythroleukemia cells maintained in RPMI 1640 medium with 25 mM HEPES buffer and 5% fetal calf serum. The cells are incubated at 37° C.

Histones are isolated from cells after incubation for periods of 2 and 24 hours. The cells are centrifuged for 5 minutes at 2000 rpm in the Sorvall SS34 rotor and washed once with phosphate buffered saline. The pellets are suspended in 10 ml lysis buffer (10 mM Tris, 50 mM sodium bisulfite, 1% Triton X-100, 10 mM magnesium chloride, 8.6% sucrose, pH 6.5) and homogenized with six strokes of a Teflon pestle. The solution is centrifuged and the pellet washed once with 5 ml of the lysis buffer and once with 5 ml 10 mM Tris, 13 mM EDTA, pH 7.4. The pellets are extracted with 2×1 mL 0.25N HCl. Histones are precipitated from the combined extracts by the addition of 20 mL acetone and refrigeration overnight. The histones are pelleted by centrifuging at 5000 rpm for 20 minutes in the Sorvall SS34 rotor. The pellets are washed once with 5 mL acetone and protein concentration are quantitated by the Bradford procedure.

Separation of acetylated histones is usually performed with an acetic acid-urea polyacrylamide gel electrophoresis procedure. Resolution of acetylated H4 histones is achieved with 6,25N urea and no detergent as originally described by Panyim and Chalkley, *Arch. Biochem. Biophys.* 130, 337–346, 1969. 25 µg total histones are applied to a slab gel which is run at 20 ma. The run is continued for a further two hours after the Pyronon Y tracking dye has run off the gel. The gel is stained with Coomassie Blue R. The most rapidly migrating protein band is the unacetylated H4 histone followed by bands with 1, 2, 3 and 4 acetyl groups which can be quantitated by densitometry. The procedure for densitometry involves digital recording using the Alpha Imager 2000, enlargement of the image using the PHOTOSHOP program (Adobe Corp.) on a MACINTOSH computer (Apple Corp.), creation of a hard copy using a laser printer and densitometry by reflectance using the Shimadzu CS9000U densitometer. The percentage of H4 histone in the various acetylated states is expressed as a percentage of the total H4 histone.

The concentration of a compound of the invention required to decrease the unacetylated H4 histone by 50% (i.e., $EC_{50}$) can then be determined from data obtained using different concentrations of test compounds.

Histone deacetylase inhibitory activity can be measured based on procedures described by Hoffmann et al., *Nucleic Acids Res.*, 27, 2057–2058 (1999). See Example 30 below. Briefly, the assay starts with incubating the isolated histone deacetylase enzyme with a compound of the invention, followed by the addition of a fluorescent-labeled lysine substrate (contains an amino group at the side chain which is available for acetylation). HPLC is used to monitor the labeled substrate. The range of activity of each test compound is preliminarily determined using results obtained from HPLC analyses. $IC_{50}$ values can then be determined from HPLC results using different concentrations of compounds of this invention. All assays are duplicated or triplicated for accuracy. The histone deacetylase inhibitory activity can be compared with the increased activity of acetylated histone for confirmation.

Compounds of this invention are also evaluated for effects on treating X-linked adrenoleukodystrophy (X-ALD), a peroxisomal disorder with impaired very long-chain fatty acid (VLCFA) metabolism. In such an assay, cell lines derived from human primary fibroblasts and (EBV-transformed lymphocytes) derived from X-ALD patients grown in RPMI are employed. Tissue culture cells are grown in the presence or absence of test compounds. For VLCFA measurements, total lipids are extracted, converted to methyl esters, purified by TLC and subjected to capillary GC analysis as described in Moser et al., *Technique in Diagnostic Biochemical Genetics: A Laboratory Manual* (ed. A., H. F.) 177–191 (Wiley-Liss, New York, 1991). C24:0 β-oxidation activity of lyophoclastoid cells are determined by measuring their capacity to degrade $[1-^{14}C]$-C24:0 fatty acid to water-soluble products as described in Watkins et al., *Arch. Biochem. Biophys.* 289, 329–336 (1991). The statistical significance of measured biochemical differences between untreated and treated X-ALD cells can be determined by a two-tailed Student's t-test. See Example 31 below.

Further, compounds of the present invention are evaluated for their effects in treating cystic fibrosis (CF). Since the initial defect in the majority of cases of CF is the inability of mutant CF protein (CFTR) to fold properly and exit the ER, compounds of the invention are tested to evaluate their efficacy in increasing the trafficking of the CF protein out of the ER and its maturation through the Golgi. During its biosynthesis, CFTR is initially synthesized as a nascent polypeptide chain in the rough ER, with a molecular weight of around 120 kDa (Band A). It rapidly receives a core glycosylation in the ER, giving it a molecular weight of around 140 kDa (Band B). As CFTR exits the ER and matures through the Golgi stacks, its glycosylation is modified until it achieves a terminal mature glycosylation, affording it a molecular weight of around 170 kDa (Band C). Thus, the extent to which CFTR exits the ER and traverses the Golgi to reach the plasma membrane may be reflected in the ratio of Band B to Band C protein. CFTR is immunoprecipitated from control cells, and cells exposed to test compounds. Both wt CFTR and ΔF508 CFTR expressing cells are tested. Following lysis, CFTR are immunoprecipitated using various CFTR antibodies. Immunoprecipitates are then subjected to in vitro phosphorylation using radioactive ATP and exogenous protein kinase A. Samples are subsequently solubilized and resolved by SDS-PAGE. Gels are then dried and subject to autoradiography and phosphor image analysis for quantitation of Bands B and C are determined on a BioRad personal fix image station. See Example 32 below.

Furthermore, compounds of this invention can be used to treat homozygous β thalassemia, a disease in which there is inadequate production of β globin leading to severe anemia. See Collins et al., *Blood,* 85(1), 43–49 (1995).

Still further, compounds of the present invention are evaluated for their use as antiprotozoal or antiparasitic agents. The evaluation can be conducted using parasite cultures (e.g., Asexual *P. falciparum*). See Trager, W. & Jensen, J. B. *Science* 193, 673–675 (1976). Test compounds of the invention are dissolved in dimethyl sulfoxide (DMSO) and added to wells of a flat-bottomed 96-well microtitre plate containing human serum. Parasite cultures are then added to the wells, whereas control wells only contain parasite cultures. After at least one invasion cycle, and addition of labeled hypoxanthine monohydrochloride, the level of incorporation of labeled hypoxanthine is detected. $IC_{50}$ values can be calculated from data using a non-linear regression analysis.

The toxicity of a compound described herein is evaluated when a compound of the invention is administered by single intraperitoneal dose to test mice. See Example 33 below. After administration of a predetermined dose to three groups of test mice and untreated controls, mortality/morbidity checks are made daily. Body weight and gross necropsy findings are also monitored. For reference, see Gad, S. C. (ed.), *Safety Assessment for Pharmaceuticals* (Van Nostrand Reinhold, New York, 1995).

Without further elaboration, it is believed that one skilled in the art can, based on the description herein, utilize the present invention to its fullest extent. The following specific examples, which described syntheses, screening, and biological testing of various compounds of this invention, are therefore, to be construed as merely illustrative, and not limitative of the remainder of the disclosure in any way whatsoever. All publications recited herein, including patents, are hereby incorporated by reference in their entirety.

EXAMPLE 1

Synthesis of 3-methyl-5-phenyl-2,4-pentadienoic acid

To a cooled (−10 to −5° C.) 165 mL of 3 M solution of methyl magnesium iodide in ether was added dropwise a solution of ethyl trans-cinnamate (25.0 g) in 200 mL of anhydrous ether. The reaction was warmed to room temperature and stirred overnight. The mixture was then heated up to 33° C. under reflux for two hours and cooled to 0° C. A white solid was formed during cooling and water (105 mL) was gradually added to dissolve the white precipitate followed by an additional 245 mL of saturated aqueous ammonium chloride solution. The mixture was then stirred until the solids were completely dissolved and extracted with 100 mL of ether three times. The combined extract was washed with 100 mL of water, dried over anhydrous sodium sulfate and filtered. The solvent was evaporated to give 22.1 g of the desired 4-phenyl-2-methyl-3-buten-2-ol as an oil which was used in the next step without further purification. $^1$H NMR (CDCl$_3$, 300 MHz), δ(ppm) 7.41 (m, 5H), 6.58 (d, 1H), 6.34 (d, 1H), 1.41 (broad s, 6H).

Dimethylformamide (DMF, anhydrous, 25 mL) was cooled to 0–5° C. and phosphorus oxychloride (16.4 mL) was added dropwise over a period of an hour. The resulting solution was added dropwise to a cooled (0–5° C.) solution of 4-phenyl-2-methyl-3-buten-2-ol (0.14 mol) in 60 mL of anhydrous DMF over a period of an hour. The reaction mixture was then warmed to room temperature, gradually heated up to 80° C., stirred at 80° C. for three hours and cooled to 0–5° C. To the cooled reaction solution was added dropwise a solution of sodium acetate (80 g) in deionized water (190 mL) over a period of two hours. The mixture was then reheated to 80° C., stirred at 80° C. for an additional 10 minutes, cooled down to room temperature and extracted with ether (300 mL) twice. The combined extract was washed with water (200 mL), dried over anhydrous sodium sulfate, filtered and concentrated in vacuum to yield 16.7 g of the desired 3-methyl-5-phenyl-2,4-pentadienal as a liquid which was used in the next step without further purification.

To a stirred solution of 3-methyl-5-phenyl-2,4-pentadienal (16.5 g) in ethanol (330 mL) was added dropwise a solution of silver nitrate (19.28 g) in water (160 mL) followed by dropwise addition of an aqueous sodium hydroxide (25 g, 80 mL) solution. The resulting mixture was allowed to stir for an additional five hours and then filtered. The solid was washed with ethanol. The combined filtrate was concentrated in vacuum. The residue was dissolved in water (200 mL). The aqueous solution was extracted with ether (300 mL) twice and acidified with 6 N hydrochloric acid (74 mL). The solid formed was filtered and recrystallized from methanol (40 mL) to yield 2.65 g of the desired 3-methyl-5-phenyl-2,4-pentadienoic acid. $^1$H NMR (acetone-d$_6$, 300 MHz), δ(ppm) 7.60 (d, 2H), 7.35 (m, 3H), 7.06 (m, 2H), 6.02 (broad s, 1H), 2.50 (s, 3H).

EXAMPLE 2

Synthesis of 4-methyl-5-phenyl-2,4-pentadienoic acid

Butyllithium (135 mL of 2.5 N solution) was added to 600 mL of anhydrous tetrahydrofuran (THF) at −65° C. A solution of diethylphosphonoacetic acid (30.5 g) in 220 mL of anhydrous THF was added dropwise to the stirred solution at −65° C. over a period of 60 minutes. The resulting solution was stirred at −65° C. for an additional 30 minutes and then a solution of α-methyl-trans-cinnamaldehyde (23.2 g) in 100 mL of anhydrous THF was added to the reaction at −65° C. over a period of 70 minutes. The reaction was stirred for one hour, allowed to warm to room temperature and then stirred overnight. The reaction was then acidified with 5% hydrochloric acid (125 mL) to a pH of 2.8. The aqueous layer was extracted with 100 mL of ether twice and with 100 mL of ethyl acetate once. The combined organic extract was dried over anhydrous sodium sulfate, filtered and concentrated under vacuum. The crude material was dissolved in 100 mL of hot methanol and then refrigerated overnight. The crystals formed were filtered and dried under vacuum to afford 25.8 g of the desired 4-methyl-5-phenyl-2,4-pentadienoic acid. $^1$H NMR (acetone-d$_6$, 300 MHz), δ(ppm) 7.53 (d, 1H), 7.43 (m, 4H), 7.37 (dd, 1H), 6.97 (broad s, 1H), 6.02 (d, 1H), 2.07 (s, 3H).

EXAMPLE 3

Synthesis of 4-chloro-5-phenyl-2,4-pentadienoic acid

Butyllithium (50 mL of 2.5 N solution) was added to 250 mL of anhydrous tetrahydrofuran (THF) at −65° C. A solution of diethylphosphonoacetic acid (11.4 g) in 90 mL of anhydrous THF was added dropwise to the stirred solution at −65° C. The resulting solution was stirred at −65° C. for an additional 40 minutes and then a solution of α-chlorocinnamaldehyde (10.0 g) in 60 mL of anhydrous THF was added to the reaction at −65° C. over a period of 95 minutes. The reaction was stirred for one hour, allowed to warm to room temperature and then stirred overnight. The reaction was then acidified with 5% hydrochloric acid (48 mL) to a pH of 3.9. The aqueous layer was extracted with 50 mL of ether twice and with 50 mL of ethyl acetate once. The combined organic extract was dried over anhydrous sodium sulfate, filtered and concentrated under vacuum. The crude material was dissolved in 30 mL of hot methanol and then refrigerated overnight. The crystals formed were filtered and dried under vacuum to afford 9.2 g of the desired 4-chloro-5-phenyl-2,4-pentadienoic acid. $^1$H NMR (acetone-d$_6$, 300 MHz), δ(ppm) 7.86 (d, 2H), 7.60 (d, 1H), 7.45 (m, 3H), 7.36 (broad s, 1H), 6.32 (d, 1H).

EXAMPLE 4

Synthesis of 5-phenyl-2-ene-4-pentynoic acid

Butyllithium (16 mL of 2.5 N solution) was added to 75 mL of anhydrous tetrahydrofuran (THF) at −65° C. A solution of diethylphosphonoacetic acid (3.6 g) in 25 mL of anhydrous THF was added dropwise to the stirred solution at −65° C. over a period of 15 minutes. The resulting solution was stirred at −65° C. for an additional 30 minutes and then a solution of phenylpropargyl aldehyde (2.5 g) in 20 mL of anhydrous THF was added to the reaction at −65° C. over a period of 20 minutes. The reaction was stirred for one hour, allowed to warm to room temperature and then stirred overnight. The reaction was then acidified with 6 N hydrochloric acid (5 mL) to a pH of 1.0. The aqueous layer was extracted with 75 mL of ethyl acetate three times. The combined organic extract was dried over anhydrous sodium sulfate, filtered and concentrated under vacuum. The crude material was recrystallized with chloroform:ether (90:10) and then refrigerated overnight. The crystals were filtered and dried under vacuum to afford 1.1 g of the desired 5-phenyl-2-ene-4-pentynoic acid. $^1$H NMR (acetone-$d_6$, 300 MHz), $\delta$(ppm) 7.50 (m, 5H), 6.98 (d, 1H), 6.35 (d, 1H).

EXAMPLE 5

Synthesis of 5-(p-dimethylaminophenyl)-2,4-pentadienoic acid

Butyllithium (24 mL of 2.5 N solution) was added to 120 mL of anhydrous tetrahydrofuran (THF) at −65° C. A solution of diethylphosphonoacetic acid (5.5 g) in 45 mL of anhydrous THF was added dropwise to the stirred solution at −65° C. over a period of one hour. The resulting solution was stirred at −65° C. for an additional 30 minutes and then a solution of p-dimethylaminocinnamaldehyde (5.0 g) in 80 mL of anhydrous THF was added to the reaction at −65° C. over a period of 30 minutes. The reaction was stirred for one hour, allowed to warm to room temperature and then stirred overnight. The reaction was then quenched with 400 mL of water and extracted with 300 mL of ethyl acetate three times. The aqueous layer was acidified with 5% hydrochloric acid (11 mL) to a pH of 6.1. The solid formed was filtered, washed with 75 mL of water and dried to yield 3.83 g of the desired 5-(p-dimethylaminophenyl)-2,4-pentadienoic acid. $^1$H NMR (DMSO-$d_6$, 300 MHz), $\delta$(ppm) 7.34 (m, 3H), 6.82 (m, 2H), 6.70 (d, 2H), 5.84 (d, 1H), 2.94 (s, 6H).

EXAMPLE 6

Synthesis of 5-(2-furyl)-2,4-pentadienoic acid

Butyllithium (70 mL of 2.5 N solution) was added to 350 mL of anhydrous tetrahydrofuran (THF) at −65° C. A solution of diethylphosphonoacetic acid (15.9 g) in 130 mL of anhydrous THF was added dropwise to the stirred solution at −65° C. over a period of 75 minutes. The resulting solution was stirred at −65° C. for an additional 30 minutes and then a solution of trans-3-(2-furyl)acrolein (10.0 g) in 85 mL of anhydrous THF was added to the reaction at −65° C. over a period of 2 hours. The reaction was allowed to warm to room temperature and stirred overnight. The reaction was then acidified with 5% hydrochloric acid (85 mL) to a pH of 3.5 followed by addition of 30 mL of water. The aqueous layer was extracted with 50 mL of ether twice and with 50 mL of ethyl acetate once. The combined organic extract was dried over anhydrous sodium sulfate, filtered and concentrated under vacuum to give an oil. The crude oil was dissolved in 45 mL of hot methanol and then refrigerated overnight. The crystals formed were filtered and dried under vacuum to afford 9.2 g of the desired 5-(2-furyl)-2,4-pentadienoic acid. $^1$H NMR (acetone-$d_6$, 300 MHz), $\delta$(ppm) 7.64 (broad s, 1H), 7.42 (m, 1H), 6.86 (m, 2H), 6.58 (m, 2H), 6.05 (d, 1H).

EXAMPLE 7

Synthesis of 6-phenyl-3,5-hexadienoic acid

Triphenylphosphine (178.7 g) and 3-chloropropionic acid (73.9 g) were mixed in a 1-liter 3-neck round bottom flask equipped with a mechanical stirrer, reflux condenser with a nitrogen inlet and a thermocouple. The mixture was heated to 145° C. under nitrogen and stirred for 2 hours. The reaction was then cooled to 70° C. Ethanol (550 mL) was added and the mixture was refluxed at 80° C. until complete dissolution. The solution was cooled to room temperature and ether (900 mL) was added. The mixture was placed in the freezer overnight. The solids were collected by filtration and dried under vacuum to afford 217 g of 3-(triphenylphosphonium)propionic acid chloride as a white solid which was used in the next step without further purification.

Sodium hydride (12.97 g) in an oven dried 5-liter 3-neck round bottom flask equipped with a mechanical stirrer and a thermocouple was cooled to 0–5° C. in an ice bath. A solution of 3-(triphenylphosphonium)propionic acid chloride (100.0 g) and trans-cinnamaldehyde (34 mL) in 400 mL each of anhydrous dimethyl sulfoxide and tetrahydrofuran was added over a period of 3 hours. The reaction was then allowed to warm to room temperature and stirred overnight. The reaction mixture was cooled to 0–5° C. in an ice bath and water (1.6 liters) was added dropwise. The aqueous solution was acidified with 12 N hydrochloric acid (135 mL) to a pH of 1 and extracted with ethyl acetate (1.6 liters) twice. The combined organic layers was washed with water (1000 mL) three times, dried over anhydrous sodium sulfate and concentrated under vacuum to afford a yellow oil. The crude oil was dissolved in 125 mL of methylene chloride and chromatographed on a Biotage 75L silica gel column and eluted with methylene chloride:ether (9:1). The fractions containing the desired product were combined and the solvents were removed under vacuum to afford 10.38 g of 6-phenyl-3,5-hexadienoic acid. $^1$H NMR (CDCl$_3$, 300 MHz), $\delta$(ppm) 7.33 (m, 5H), 6.80 (m, 1H), 6.53 (d, 1H), 6.34 (m, 1H), 5.89 (m, 1H), 3.25 (d, 2H).

EXAMPLE 8

Synthesis of 7-phenyl-2,4,6-heptatrienoic acid

To a cooled (0–55° C.) 927 mL of 1 M solution of phenyl magnesium bromide in tetrahydofuran was added dropwise a solution of crotonaldehyde (65.0 g) in 130 mL of anhydrous ether over a period of 2 hours and 45 minutes. The reaction was stirred for an additional 45 minutes and then warmed to room temperature. After four more hours of stirring, saturated ammonium chloride aqueous solution (750 mL) was added to the reaction. The mixture was extracted with 750 mL of ether twice. The combined extract was dried over anhydrous potassium carbonate and filtered. The solvent was evaporated to give 135.88 g (99.9%) of the desired 1-phenyl-2-buten-1-ol as an oil which was used in the next step without further purification.

1-Phenyl-2-buten-1-ol (135.88 g) was dissolved in 2300 mL of dioxane and treated with 2750 mL of dilute hydrochloric acid (2.3 mL of concentrated hydrochloric acid in 2750 mL of water) at room temperature. The mixture was stirred overnight and then poured into 4333 mL of ether and neutralized with 2265 mL of saturated aqueous sodium bicarbonate. The aqueous phase was extracted with 1970 mL of ether. The combined extract was dried over anhydrous potassium carbonate. Evaporation of the solvent followed by Kugelrohr distillation at 30° C. for 30 minutes afforded 131.73 g (96.8%) of the desired 4-phenyl-3-buten-2-ol as an oil which was used in the next step without further purification.

Dimethylformamide (DMF, anhydrous, 14 mL) was cooled to 0–5° C. and phosphorus oxychloride (8.2 mL) was added dropwise over a period of 40 minutes. The resulting solution was added dropwise to a cooled (0–5° C.) solution of 4-phenyl-3-buten-2-ol (10 g) in 32 mL of anhydrous DMF over a period of an hour. The reaction mixture was warmed to room temperature over a 35-minute period and then gradually heated up to 80° C. over a period of 45 minutes. The reaction was stirred at 80° C. for three hours and then cooled to 0–5° C. To the cooled reaction solution was added dropwise a solution of sodium acetate (40 g) in deionized water (100 mL) over a period of one hour. The mixture was then reheated to 80° C., stirred at 80° C. for an additional 10 minutes, cooled down to room temperature and extracted with ether (100 mL) twice. The combined extract was washed with brine (100 mL), dried over anhydrous sodium sulfate, filtered and concentrated under vacuum to yield 8.78 g of the desired 5-phenyl-2,4-pentadienal as a liquid which was used in the next step without further purification. $^1$H NMR (CDCl$_3$, 300 MHz), δ(ppm) 7.51 (m, 2H), 7.37 (m, 3H), 7.26 (m, 1H), 7.01 (m, 2H), 6.26 (m, 1H).

Butyllithium (12.8 mL of 2.5 N solution) was added to 65 mL of anhydrous tetrahydrofuran (THF) at −65° C. A solution of diethylphosphonoacetic acid (2.92 g) in 25 mL of anhydrous THF was added dropwise to the stirred solution at −65° C. The resulting solution was stirred at −65° C. for an additional 30 minutes and then a solution of 5-phenyl-2,4-pentadienal (2.4 g) in 15 mL of anhydrous THF was added to the reaction at −65° C. The reaction was stirred for one hour, allowed to warm to room temperature and then stirred overnight. To the reaction was added 30 mL of water, acidified with 5% hydrochloric acid (14 mL) to a pH of 4.7 and then added an additional 20 mL of water. The aqueous layer was extracted with 10 mL of ether twice and with 10 mL of ethyl acetate once. The combined organic extract was dried over anhydrous sodium sulfate, filtered and concentrated under vacuum. The crude material was dissolved in 50 mL of hot methanol and then refrigerated overnight. The crystals formed were filtered and dried under vacuum to afford 2.4 g of the desired 7-phenyl-2,4,6-heptatrienoic acid. $^1$H NMR (DMSO-d$_6$, 300 MHz), δ(ppm) 7.52 (m, 2H), 7.33 (m, 4H), 7.06 (m, 1H), 6.86 (m, 2H), 6.58 (m, 1H), 5.95 (d, 1H).

EXAMPLE 9

Synthesis of 8-phenyl-3,5,7-octatrienoic acid

A solution of 5-phenyl-2,4-pentadienal (15 g) and 3-(triphenylphosphonium)-propionic acid chloride (35.2 g) in 140 mL each of anhydrous tetrahydrofuran and anhydrous dimethyl sulfoxide was added dropwise to sodium hydride (4.6 g) at 0–5° C. under nitrogen over a period of four hours. The reaction was allowed to warm to room temperature and stirred overnight. The reaction mixture was cooled to 0–5° C. and water (280 mL) was added dropwise over a period of 30 minutes. The aqueous layer was extracted with ethyl acetate (280 mL) twice, acidified with 12 N hydrochloric acid (24 mL) to a pH of 1, extracted again with ethyl acetate (280 mL) twice. The combined organic layers were washed with water (500 mL) twice, dried over anhydrous sodium sulfate and concentrated under vacuum to give an oil. The oily crude product was chromatographed on a Biotage 40M silica gel column and eluted with methylene chloride:ethyl acetate (95:5). The fractions containing the desired product were combined and the solvents were removed under vacuum to afford 0.7 g of 8-phenyl-3,5,7-octatrienoic acid. $^1$H NMR (acetone-d$_6$, 300 MHz), δ(ppm) 7.46 (m, 2H), 7.26 (m, 3H), 6.95 (m, 1H), 6.60 (d, 1H), 6.34 (m, 3H), 5.87 (m, 1H), 3.17 (d, 2H).

EXAMPLE 10

Synthesis of Potassium 2-oxo-6-phenyl-3,5-Hexadienoate

A solution of trans-cinnamaldehyde (26.43 g) and pyruvic acid (11.9 mL) in 10 mL of methanol was stirred and chilled to 0–5° C. in an ice bath. To the chilled solution was added 35 mL of potassium hydroxide (16.83 g in 50 mL of methanol) over a period of 20 minutes. The remaining methanolic potassium hydroxide was added rapidly and the ice bath was removed. The solution changed from a yellow to a dark orange and the precipitate was formed. The reaction mixture was chilled in the refrigerator overnight and the solid was collected by filtration, washed with 50 mL of methanol three times, 50 mL of ether and then air dried to afford 29.3 g of the desired 2-oxo-6-phenyl-3,5-hexadienoate as a yellow solid (61.0%). $^1$H NMR (DMSO-d$_6$/D$_2$O, 300 MHz), δ(ppm) 7.48 (d, 2H), 7.28 (m, 4H), 7.12 (d, 2H), 6.27 (d, 1H).

EXAMPLE 11

Synthesis of Potassium 2-oxo-8-phenyl-3,5,7-octatrienoate

To a cooled (0–55° C.) 927 mL of 1 M solution of phenyl magnesium bromide in tetrahydofuran was added dropwise a solution of crotonaldehyde (65.0 g) in 130 mL of anhydrous ether over a period of 2 hours and 45 minutes. The reaction was stirred for an additional 45 minutes and then warmed to room temperature. After four more hours of stirring, saturated ammonium chloride aqueous solution (750 mL) was added to the reaction. The mixture was extracted with 750 mL of ether twice. The combined extract was dried over anhydrous potassium carbonate and filtered. The solvent was evaporated to give 135.88 g (99.9%) of the desired 1-phenyl-2-buten-1-ol as an oil which was used in the next step without further purification.

1-Phenyl-2-buten-1-ol (135.88 g) was dissolved in 2300 mL of dioxane and treated with 2750 mL of dilute hydrochloric acid (2.3 mL of concentrated hydrochloric acid in 2750 mL of water) at room temperature. The mixture was stirred overnight and then poured into 4333 mL of ether and neutralized with 2265 mL of saturated sodium bicarbonate. The aqueous phase was extracted with 1970 mL of ether. The combined extract was dried over anhydrous potassium carbonate. Evaporation of the solvent followed by Kugelrohr distillation at 30° C. for 30 minutes afforded 131.73 g (96.8%) of the desired 4-phenyl-3-buten-2-ol as an oil which was used in the next step without further purification.

Dimethylformamide (DMF, anhydrous, 14 mL) was cooled to 0–5° C. and phosphorus oxychloride (8.2 mL) was added dropwise over a period of 40 minutes. The resulting solution was added dropwise to a cooled (0–5° C.) solution of 4-phenyl-3-buten-2-ol (10 g) in 32 mL of anhydrous DMF over a period of all hour. The reaction mixture was warmed to room temperature over a 35-minute period and then gradually heated up to 80° C. over a period of 45 minutes. The reaction was stirred at 80° C. for three hours and then cooled to 0–5° C. To the cooled reaction solution was added dropwise a solution of sodium acetate (40 g) in deionized water (100 mL) over a period of one hour. The mixture was then reheated to 80° C., stirred at 80° C. for an additional 10 minutes, cooled down to room temperature and extracted with ether (100 mL) twice. The combined extract was washed with brine (100 mL), dried over anhydrous sodium sulfate, filtered and concentrated under vacuum to yield 8.78 g of the desired 5-phenyl-2,4-pentadienal as a liquid which was used in the next step without further purification. $^1$H NMR (CDCl$_3$, 300 MHz), δ(ppm) 7.51 (m, 2H), 7.37 (m, 3H), 7.26 (m, 1H), 7.01 (m, 2H), 6.26 (m, 1H).

A solution of 5-phenyl-2,4-pentadienal (6.70 g) and pyruvic acid (3.0 mL) in 5 mL of methanol was stirred and chilled to 0–5° C. in an ice bath. To the chilled solution was added a solution of 35 mL of potassium hydroxide (3.5 g) in 10 mL of methanol dropwise over a period of 30 minutes. The remaining methanolic potassium hydroxide was added rapidly and the ice bath was removed. The reaction was allowed to warm to room temperature and stirred for another hour. The flask was then refrigerated overnight. The solid was collected by filtration, washed with 15 mL of methanol three times, 15 mL of ether and then air dried to afford 6.69 g of potassium 2-oxo-8-phenyl-3,5,7-octatrienoate as a yellow solid. $^1$H NMR (DMSO-d$_6$, 300 MHz), δ(ppm) 7.52 (d, 2H), 7.32 (m, 3H), 7.10 (m, 2H), 6.83 (dd, 2H), 6.57 (dd, 1H), 6.13 (d, 1H).

EXAMPLE 12

Synthesis of cinnamoylhydroxamic acid

Triethylamine (TEA, 17.6 mL) was added to a cooled (0–5° C.) solution of trans-cinnamic acid (15.0 g) in 200 mL of anhydrous dimethylformamide. To this solution was added dropwise isobutyl chloroformate (16.4 mL). The reaction mixture was stirred for 30 minutes and hydroxylamine hydrochloride (17.6 g) was added followed by dropwise addition of 35 mL of TEA at 0–5° C. The reaction was allowed to warm to room temperature and stirred overnight. The reaction was quenched with 250 mL of 1% (by weight) citric acid solution and 50 mL of 5% (by weight) citric acid solution and then extracted with 200 mL of methylene chloride twice and 200 mL of ether once. The solvents were removed under vacuum. The residue was triturated with 125 mL of water, filtered, washed with 25 mL of water and dried under vacuum to give a tan solid. The crude product was chromatographed on a Biotage 75S column and eluted with methylene chloride:acetonitrile (80:20). The fractions containing the desired product were combined and the solvent was removed under vacuum to yield 4.1 g of cinnamoylhydroxamic acid. $^1$H NMR (DMSO-d$_6$, 300 MHz), δ(ppm) 7.48 (m, 6H), 6.49 (d, 1H).

EXAMPLE 13

Synthesis of N-methyl-cinnamoylhydroxamic acid

A solution of cinnamoyl chloride (5 g) in 50 mL of methylene chloride was added dropwise to a solution of N-methylhydroxylamine hydrochloride (5 g) and 12 mL of 40% sodium hydroxide in 50 mL of water cooled to 0–5° C. The reaction mixture was stirred for two hours. The aqueous layer was acidified with concentrated hydrochloric acid. The precipitate was collected by filtration and dried under vacuum to afford 2.8 g of the desired N-methyl-cinnamoylhydroxamic acid as a white solid. $^1$H NMR (DMSO-d$_6$, 300 MHz), δ(ppm) 7.66 (d, 2H), 7.53 (d, 1H), 7.42 (m, $^3$H), 7.26 (d, 1H), 3.22 (s, 3H).

EXAMPLE 14

Synthesis of 5-phenyl-2,4-pentadienoylhydroxamic acid

Triethylamine (TEA, 29 mL) was added to a cooled (0–5° C.) solution of 5-phenyl-2,4-pentadienoic acid (29.0 g) in 300 mL of anhydrous dimethylformamide. To this solution was added dropwise isobutyl chloroformate (27.0 mL). The reaction mixture was stirred for 15 minutes and hydroxylamine hydrochloride (28.92 g) was added followed by dropwise addition of 58 mL of TEA over a period of 60 minutes at 0–5° C. The reaction was allowed to warm to room temperature and stirred overnight. The reaction was then poured into 450 mL of a 1% (by weight) solution of citric acid and then extracted with 200 mL of methylene chloride twice and 500 mL of ether once. The solvents were removed under vacuum to give an oil. The crude oil was crystallized with 200 mL of hot acetonitrile to give a tan solid. The tan solid was recrystallized from 60 mL of hot acetonitrile to afford 12.5 g of the desired 5-phenyl-2,4-pentadienoylhydroxamic acid. $^1$H NMR (DMSO-d$_6$, 300 MHz), δ(ppm) 7.56 (d, 2H), 7.31 (m, 4H), 7.03 (m, 2H), 6.05 (s, 1H).

EXAMPLE 15

Synthesis of N-methyl-5-phenyl-2,4-pentadienoylhydroxamic acid

5-Phenyl-2,4-pentadienoic acid (6 g) and oxalyl chloride (6.1 mL) were dissolved in 50 mL of methylene chloride and 0.2 mL of dimethylformamide was added. The reaction was stirred for three hours, concentrated under vacuum and then co-evaporated with 100 mL of chloroform to remove oxalyl chloride. The crude 5-phenyl-2,4-pentadienoic acid chloride was used in the next step without further purification.

5-Phenyl-2,4-pentadienoic acid chloride was dissolved in 50 mL of methylene chloride and added to a solution of 13.8 mL of 40% sodium hydroxide in 50 mL of water at 0–5° C. The resulting solution was stirred for two hours and then acidified to a pH of 4 with concentrated hydrochloric acid. The precipitate was collected by filtration and dried under vacuum to afford 4.2 g of N-methyl-5-phenyl-2,4-pentadienoylhydroxamic acid. $^1$H NMR (DMSO-d$_6$, 300 MHz), δ(ppm) 7.57 (d, 2H), 7.35 (m, 4H), 7.19 (m, 1H), 6.99 (d, 1H), 6.82 (d, 1H), 3.21 (s, 3H).

EXAMPLE 16

Synthesis of 3-methyl-5-phenyl-2,4-pentadienoylhydroxamic acid

Triethylamine (TEA, 1.8 mL) was added to a cooled (0–5° C.) solution of 3-methyl-5-phenyl-2,4-pentadienoic acid (2.0 g) in 20 mL of anhydrous dimethylformamide. To this solution was added dropwise isobutyl chloroformate (1.7 mL) over a period of 15 minutes. The reaction mixture was stirred for 30 minutes and hydroxylamine hydrochloride (1.85 g) was added followed by dropwise addition of 3.7 mL of TEA over a period of 35 minutes at 0–5° C. The reaction was allowed to warm to room temperature and stirred overnight. To the stirred reaction mixture at room temperature was added 20 mL of a 1% (by weight) solution of citric acid followed by 75 mL of water. The mixture was stirred for 30 minutes and then filtered. The filtered cake was washed with 30 mL of water and dried in vacuum to afford 1.49 g of the desired 3-methyl-5-phenyl-2,4-pentadienoylhydroxamic acid in 69% yield. $^1$H NMR (DMSO-d$_6$, 300 MHz), δ(ppm) 7.55 (d, 2H), 7.30 (m, 3H), 6.89 (broad s, 2H), 5.83 (s, 1H), 2.38 (s, 3H).

EXAMPLE 17

Synthesis of 4-methyl-5-phenyl-2,4-pentadienoylhydroxamic acid

Triethylamine (TEA, 6.5 mL) was added to a cooled (0–5° C.) solution of 4-methyl-5-phenyl-2,4-pentadienoic acid (7.0 g) in 75 mL of anhydrous dimethylformamide. To this solution was added dropwise isobutyl chloroformate (6.0 mL) over a period of 60 minutes. The reaction mixture was stirred for 15 minutes and hydroxylamine hydrochloride (6.5 g) was added followed by dropwise addition of 13 mL of TEA over a period of 60 minutes at 0–5° C. The reaction was allowed to warm to room temperature and stirred overnight. To the stirred reaction mixture at room temperature was added 130 mL of a 1% (by weight) solution of citric acid followed by 50 mL of water. The mixture was stirred for 30 minutes and then filtered. The filtered cake was recrystallized from hot acetonitrile to afford 4.4 g of the desired 4-methyl-5-phenyl-2,4-pentadienoylhydroxamic acid. $^1$H NMR (DMSO-$d_6$, 300 MHz), δ(ppm) 7.37 (m, 6H), 6.91 (s, 1H), 6.02 (d, 1H), 1.99 (s, 3H).

EXAMPLE 18

Synthesis of 4-chloro-5-phenyl-2,4-pentadienoylhydroxamic acid

Triethylamine (TEA, 2.5 mL) was added to a cooled (0–5° C.) solution of 4-chloro-5-phenyl-2,4-pentadienoic acid (3.0 g) in 30 mL of anhydrous dimethylformamide. To this solution was added dropwise isobutyl chloroformate (2.3 mL) over a period of 15 minutes. The reaction mixture was stirred for 30 minutes and hydroxylamine hydrochloride (2.5 g) was added followed by dropwise addition of 5.0 mL of TEA over a period of 60 minutes at 0–5° C. The reaction was allowed to warm to room temperature and stirred overnight. The reaction was then quenched with 30 mL of a 1% (by weight) solution of citric acid followed by 115 mL of water. The mixture was stirred for 30 minutes and then filtered. The filtered cake was washed with 100 mL of water and dried under vacuum. The crude material was recrystallized from 20 mL of hot acetonitrile twice to yield 1.46 g of the desired 4-chloro-5-phenyl-2,4-pentadienoylhydroxamic acid as a solid. $^1$H NMR (DMSO-$d_6$, 300 MHz), δ(ppm) 7.75 (d, 2H), 7.40 (m, 5H), 6.31 (d, 1H).

EXAMPLE 19

Synthesis of 5-phenyl-2-ene-4-pentynoylhydroxamic acid

Triethylamine (TEA, 1.1 mL) was added to a cooled (0–5° C.) solution of 5-phenyl-2-ene-4-pentynoic acid (1.1 g) in 13 mL of anhydrous dimethylformamide. To this solution was added dropwise isobutyl chloroformate (1.0 mL). The reaction mixture was stirred for 30 minutes and hydroxylamine hydrochloride (1.1 g) was added followed by dropwise addition of 2.2 mL of TEA at 0–5° C. The reaction was allowed to warm to room temperature and stirred overnight. The reaction was quenched with 15 mL of a 1% (by weight) solution of citric acid and extracted with 30 mL of methylene chloride twice. The combined organic layer was dried over anhydrous sodium sulfate. The solvents were removed under vacuum to give an oil which in turn was triturated with 10 mL of chloroform. The solid was collected by filtration to yield 0.63 g of the desired 5-phenyl-2-ene-4-pentynoylhydroxamic acid as a white powder. $^1$H NMR (DMSO-$d_6$, 300 MHz), δ(ppm) 7.48 (m, 5H), 6.76 (d, 1H), 6.35 (d, 1H).

EXAMPLE 20

Synthesis of 5-p-dimethylaminophenyl)-2,4-pentadienoylhydroxamic acid

Triethylamine (TEA, 0.8 mL) was added to a cooled (0–5° C.) solution of 5-(p-dimethylaminophenyl)-2,4-pentadienoic acid (1.0 g) in 10 mL of anhydrous dimethylformamide. To this solution was added dropwise isobutyl chloroformate (0.7 mL). The reaction mixture was stirred for 60 minutes and hydroxylamine hydrochloride (0.8 g) was added followed by dropwise addition of 1.6 mL of TEA at 0–5° C. The reaction was allowed to warm to room temperature and stirred overnight. The reaction was quenched with 15 mL of water. The solid was filtered and dried under vacuum to yield 0.75 g of the desired 5-(p-dimethylaminophenyl)-2,4-pentadienoylhydroxamic acid. $^1$H NMR (DMSO-$d_6$, 300 MHz), δ(ppm) 7.33 (m, 3H), 6.86 (m, 2H), 6.70 (d, 2H), 5.84 (d, 1H), 2.99 (s, 6H).

EXAMPLE 21

Synthesis of 5-(2-furyl)-2,4-pentadienoylhydroxamic acid

Triethylamine (TEA, 2.1 mL) was added to a cooled (0–5° C.) solution of 5-(2-furyl)-2,4-pentadienoic acid (2.0 g) in 15 mL of anhydrous dimethylformamide. To this solution was added dropwise isobutyl chloroformate (2.0 mL) over a period of 30 minutes. The reaction mixture was stirred for 30 minutes and hydroxylamine hydrochloride (2.15 g) was added followed by dropwise addition of 4.2 mL of TEA over a period of 60 minutes at 0–5° C. The reaction was allowed to warm to room temperature and stirred overnight. To the stirred reaction mixture at room temperature was added 12 mL of a 1% (by weight) solution of citric acid followed by 46 mL of water. The mixture was stirred for 30 minutes and then filtered. The filtered cake was washed with 30 mL of water and dried in vacuum to afford 1.3 g of the desired 5-(2-furyl)-2,4-pentadienoylhydroxamic acid. $^1$H NMR (DMSO-$d_6$, 300 MHz), δ(ppm) 7.73 (broad s, 1H), 7.22 (m, 1H), 6.71 (m, 4H), 6.01 (d, 1H).

EXAMPLE 22

Synthesis of 6-phenyl-3,5-hexadienoylhydroxamic acid

Triethylamine (TEA, 1.75 mL) was added to a cooled (0–5° C.) solution of 6-phenyl-3,5-hexadienoic acid (2.0 g) in 30 mL of anhydrous dimethylformamide. To this solution was added dropwise isobutyl chloroformate (1.62 mL) over a period of 15 minutes. The reaction mixture was stirred for 15 minutes and hydroxylamine hydrochloride (1.74 g) was added followed by dropwise addition of 3.5 mL of TEA at 0–5° C. The reaction was allowed to warm to room temperature and stirred overnight. The reaction was then poured into 20 mL of 1% (by weight) aqueous citric acid solution and extracted with 20 mL of methylene chloride twice and ether once. The combined organic layer was dried over anhydrous sodium sulfate and concentrated under vacuum to give a dark red oil. The crude oil was crystallized with 10 mL of hot acetonitrile. The solid was collected by filtration and then purified on a Biotage 40S silica gel column using methylene chloride:ether (95:5) as an eluent. The fractions containing the desired product were combined and the solvent was removed to give 40 mg of 6-phenyl-3,5-hexadienoylhydroxamic acid as a tan solid (2.1%). $^1$H NMR (DMSO-$d_6$, 300 MHz), δ(ppm) 7.34 (m, 5H), 6.91 (m, 1H), 6.55 (d, 1H), 6.30 (m, 1H), 5.89 (m, 1H), 3.36 (d, 2H).

EXAMPLE 23

Synthesis of N-methyl-6-phenyl-3,5-hexadienoylhydroxamic acid

6-Phenyl-3,5-hexadienoic acid (1 g) was dissolved in 10 mL of tetrahydrofuran (THF) and treated with 0.9 g of 1,1'-carbonyldiimidazole. The reaction was stirred for 30 minutes. N-methylhydroxylamine hydrochloride (0.44 g) was neutralized with 0.29 g of sodium methoxide in 10 mL of THF and 5 mL of methanol and then filtered to remove the sodium chloride. N-methylhydroxylamine was then added to the reaction mixture and stirred overnight. The resulting mixture was partitioned between 25 mL of water and 50 mL of ethyl acetate. The ethyl acetate layer was washed with 25 mL each of 5% hydrochloric acid, saturated sodium bicarbonate and brine, dried over sodium sulfate and concentrated under vacuum to afford 0.9 g of a viscous yellow oil. The crude product was chromatographed on a Biotage 40S silica gel column and eluted with ethyl acetate:hexane (1:1). The fractions containing the desired product were combined and the solvent was removed under vacuum to yield 0.17 g of N-methyl-6-phenyl-3,5-hexadienoylhydroxamic acid. $^1$H NMR (CDCl$_3$, 300 MHz), δ(ppm) 7.38 (m, 5H), 6.80 (m, 1H), 6.60 (m, 1H), 6.35 (m, 1H), 5.89 (m, 1H), 3.24 (m, 2H), 2.92 (s, 3H).

EXAMPLE 24

Synthesis of 7-phenyl-2,4,6-heptatrienoylhydroxamic acid

Triethylamine (TEA, 24.1 mL) was added to a cooled (0–5° C.) solution of 7-phenyl-2,4,6-heptatrienoic acid (27.8 g) in 280 mL of anhydrous dimethylformamide. To this solution was added dropwise isobutyl chloroformate (22.5 mL) over a period of 75 minutes. The reaction mixture was stirred for 40 minutes and hydroxylamine hydrochloride (24.2 g) was added followed by dropwise addition of 48 mL of TEA over a period of 70 minutes at 0–5° C. The reaction was allowed to warm to room temperature and stirred overnight. To the stirred reaction mixture at room temperature was added 280 mL of a 1% (by weight) solution of citric acid followed by 1050 mL of water. The mixture was stirred for 30 minutes and then filtered. The filtered cake was washed with water (200 mL) and dried under vacuum to afford 20.5 g of the desired 7-phenyl-2,4,6-heptatrienoylhydroxamic acid. $^1$H NMR (DMSO-d$_6$, 300 MHz), δ(ppm) 7.48 (m, 2H), 7.32 (m., 2H), 7.19 (m, 2H), 7.01 (m, 1H), 6.75 (m, 2H), 6.51 (m, 1H), 5.93 (d, 1H).

EXAMPLE 25

Synthesis of 4-cyclohexylbutyroylhydroxamic acid

To a solution of hydroxylamine hydrochloride (7.3 g) in 50 mL of methanol was added 24 mL of sodium methoxide (25% wt.) dropwise at room temperature over a period of 45 minutes. To this solution was added methyl 4-cyclohexylbutyrate in 50 mL of methanol at room temperature followed by 12 mL of sodium methoxide (25% wt.) dropwise over a period of 60 minutes. The resulting mixture was stirred at room temperature overnight. The reaction was then poured into 120 mL of water and acidified to a pH of 4 with 45 mL of glacial acetic acid. Methanol was removed under vacuum. The solid formed was filtered and dried over phosphorus pentoxide to afford 8.53 g of the desired 4-cyclohexylbutyroyl-hydroxamic acid. $^1$H NMR (DMSO-d$_6$, 300 MHz), δ(ppm) 3.38 (m, 2H), 1.91 (t, 2H), 1.68 (m, 4H), 1.50 (m, 2H), 1.16 (m, 5H), 0.84 (nm, 2H).

EXAMPLE 26

Synthesis of S-benzylthioglycoloylhydroxamic acid

S-benzylthioglycolic acid (12.0 g) was dissolved in 250 mL of methanol and sparged with hydrogen chloride gas at room temperature for 20 minutes. The solvent was then removed under vacuum. Methyl S-benzylthioglycolate obtained was used in the next step without further purification.

To a solution of hydroxylamine hydrochloride (9.2 g) in 60 mL of methanol was added 30 mL of sodium methoxide (25% wt.) dropwise at room temperature over a period of 30 minutes. To this solution was added methyl S-benzylthioglycolate in 50 mL of methanol at room temperature followed by 15 mL of sodium methoxide (25% wt.) dropwise over a period of 60 minutes. The resulting mixture was stirred at room temperature overnight. The reaction was then poured into 150 mL of water and acidified to a pH of 4 with 55 mL of glacial acetic acid. Methanol was removed under vacuum. The solid formed was filtered and dried over phosphorus pentoxide to afford 8.57 g of the desired S-benzylthioglycoloyl-hydroxamic acid. $^1$H NMR (DMSO-d$_6$, 300 MHz), δ(ppm) 7.29 (m, 5H), 3.84 (s, 2H), 2.93 (s, 2H).

EXAMPLE 27

Synthesis of 5-phenylpentanoloylhydroxamic acid

5-Phenylpentanoic acid (10.0 g) was dissolved in 250 mL of methanol and sparged with hydrogen chloride gas at room temperature for 15 minutes. The solvent was then removed under vacuum. Methyl 5-phenylpentanoate obtained was used in the next step without further purification.

To a solution of hydroxylamine hydrochloride (7.8 g) in 50 mL of methanol was added 26 mL of sodium methoxide (25% wt.) dropwise at room temperature over a period of 45 minutes. To this solution was added methyl 5-phenylpentanoate in 50 mL of methanol at room temperature followed by 15 mL of sodium methoxide (25% wt.) dropwise over a period of 60 minutes. The resulting mixture was stirred at room temperature overnight. The reaction was then poured into 150 mL of water and acidified to a pH of 4 with 40 mL of glacial acetic acid. The solvents were removed under vacuum to give a yellow oil. The yellow oil was placed on a Biotage 40M silica gel column and eluted with methylene chloride:ethanol (95:5). The fractions containing the desired product as indicated by the NMR were combined. The solvents were removed under vacuum to afford 8.30 g of the desired 5-phenylpentanoylhydroxamic acid. $^1$H NMR (DMSO-d$_6$, 300 MHz), δ(ppm) 7.22 (m, 5H), 3.42 (s, 3H), 2.55 (t, 2H), 1.98 (t, 2H), 1.52 (m, 4H).

EXAMPLE 28

In vitro Efficacy Studies—Extreme Drug Resistance (EDR) Assay

The PC3 cell line was maintained in RPM1 supplemented with 10% fetal calf serum and antibiotics. Cells were suspended in 0.12% soft agar in complete medium and plated (2,000 cells per well) in different drug concentrations onto a 0.4% agarose underlayer in 24-well plates. Plating calls on agarose underlayers supports the proliferation only of the transformed cells, ensuring that the growth signal stems from the malignant component of the tumor.

All compounds were dissolved were dissolved in DMSO to 200× stock solutions. Stock solutions were diluted to 20× working solutions using the tissue culture medium, serially diluted and added to the 24-well plates. The initial range of concentrations was 1 micromolar to 200 micromolar. This concentration range was extended in the case of N-methyl-5-phenyl-2,4-pentadienoylhydroxamic acid to 10 μM-500 μM and in the case of tricostatin A to 0.001 μM to 0.3 μM.

No significant changes in pH of the culture medium were observed under the above conditions. Diluent control wells contained PC3 cells treated with DMSO, at the dilutions used for appropriate drug treatment. All experimental points were represented by two separate wells (duplicates). Four wells containing tumor cells that were not treated with drugs served as negative controls in each experiment.

Cells were incubated with drugs under standard culture conditions for 5 days. Cultures were pulsed with tritiated thymidine ($^3$H-TdR, New Life Science Products, Boston, Mass.) at 5 µCi per well for the last 48 hours of the culture period. Cell culture plates were then heated to 90° C. to liquefy the agarose, and cells were harvested onto glass fiber filters, which were then placed into counting vials containing liquid scintillation fluid. The radioactivity trapped on the filters was counted with a Beckman scintillation counter. The fraction of surviving cells was determined by comparing $^3$H-TdR incorporation in treated (experimental points) and untreated (negative control) wells. Microsoft Excel was used to organize the raw data on EDR experiments, and the SigmaPlot program was utilized to generate drug response curves. All drug response curves were as approximated as sigmoidal equations (characteristic for typical drug response curves) to fit the data. $IC_{50}$ values were determined using the approximated sigmoidal curves and expressed as mM.

$IC_{50}$ values of the test compounds of the invention range from approximately 1 µM to approximately 2000 µM.

EXAMPLE 29

Histone (Hyper)Acetylation Assay

The model used in this assay was mouse erythroleukemia cells. Specifically, the level of acetylation of H4 histones in these erythroleukemia cells was monitored. H4 histones was chosen as the target due to the ease of resolution of the variably acetylated histones. Inhibition of histone deacetylase leads to increased (hyper)acetylation of histones. Activities on histone deacetylase were examined to confirm the results of this assay. See Example 30 below.

Studies were performed with the DS19 mouse erythroleukemia cells maintained in RPMI 1640 medium with 25 mM HEPES buffer and 5% fetal calf serum. The cells were incubated at 37° C. In studies on proliferation, cell density was determined at 24 hour intervals using a hemacytometer.

Histone Isolation

Histones were isolated from cells after incubation for 2 or 24 hours. The cells were centrifuged for 5 minutes at 2,000 rpm in the Sorvall SS34 rotor and washed once with phosphate buffered saline. The pellets were suspended in 5 mL lysis buffer (10 mM Tris, 50 mM sodium bisulfite, 1% Triton X-100, 10 mM magnesium chloride, 8.6% sucrose, pH 6.5) and homogenized with six strokes of a teflon pestle. The homogenizing tubes were rinsed with 5 mL lysis buffer. The combined solutions were centrifuged and the pellets were washed once with 5 mL of the lysis buffer and once with 5 mL 10 mM Tris, 13 mM EDTA, pH 7.4. The pellets were extracted with 2×1 mL 0.25N HCl. Histones were precipitated from the combined extracts by the addition of 20 mL acetone and refrigeration overnight. The histones were pelleted by centrifuging at 5,000 rpm for 20 minutes in the Sorvall SS34 rotor. The pellets were washed once with 5 mL acetone and protein concentration was quantitated by the Bradford procedure.

Polyacrylamide Gel Electrophoresis

Separation of acetylated histones was performed with an acetic acid-urea polyacrylamide gel electrophoresis procedure as originally described by Panyim and Chalkley *Arch. Biochem. Biophys.* 130, 337–346, 1969. 25 µg histones were applied to a slab gel which was run at 20 ma. The run was continued for a further two hours after the Pyronin Y tracking dye had run off the gel. The gel was stained with Coomassie Blue R. The most rapidly migrating protein band is the unacetylated H4 histone followed by bands with 1,2,3 and 4 acetyl groups which were quantitated by densitometry.

Densitometry

Densitometry was measured through digital recording using the Alpha Imager 2000. Enlargement of the image was done using PHOTOSHOP (Adobe Corp.) on a MACINTOSH (Apple Corp.) computer. After creating a hard copy of the gel by using a laser printer, a Shimadzu CS9OOOU densitometer was used to measure densitometry by reflectance. The percentage of H4 histone in the various acetylated states was expressed as a percentage of the total H4 histone.

Results

Many of the test compounds of the invention showed $EC_{50}$ values in micromolar concentration range.

EXAMPLE 30

Histone Deacetylation Assay

The determination of the inhibition of histone deacetylase by compounds of the invention was based upon the procedure described by Hoffmann et al., *Nucleic Acids Res.* 27, 2057–2058 (1999). The histone deacetylase was isolated from rat liver as previously described in Kolle, D. et al., *Methods: A Companion to Methods in Enzymology* 15, 323–331 (1998). Compounds were initially dissolved in either ethanol or in DMSO to provide a working stock solution. The synthetic substrate used in the assay is N-(4-methyl-7-coumarinyl)-N-α(tert-butyloxy-carbonyl)-N-Ω-acetyllysineamide (MAL).

The assay was performed in a final total volume of 120 µL consisting of 100 µL of 15 mM tris-HCl buffer at pH 7.9 and 0.25 mM EDTA, 10 mM NaCl, 10% glycerol, 10 mM mercaptoethanol and the enzyme. The assay was initiated upon the addition of 10 µl of a test compound followed by the addition of a fluorescent-labeled lysine substrate to each assay tube in an ice bath for 15 minutes. The tubes were transferred to a water bath at 37° C. for an additional 90 minutes.

An initial assay was performed to determine the range of activity of each test compound. The determination of $IC_{50}$ values was made from the results of five dilutions in range according to the expected potency for each test compound. Each assay was duplicated or triplicated.

Test compounds of the invention showed potent inhibition of histone deacetylase, having $IC_{50}$ values in the low micromolar concentration range (e.g., two test compounds showed $IC_{50}$ values of 1.7 µM and 1.8 µM).

EXAMPLE 31

X-ALD Screening Assay

Cell Cultures and Drug Treatment

Cell lines derived from X-ALD human patients were grown in RPMI supplemented with fetal calf serum (10%), penicillin (100 U/mL), streptomycin (100 U/mL) and glutamine (2 mM). On day 0, cells were divided into two separate tissue culture flasks, and test compounds (2.5–250 µM final concentration, diluted from a 0.5 M stock solution in PBS, pH 7.6) was added to one flask. Cells in the second flask were grown in the absence of test compounds for the same length of time and served as controls. The media were changed every 3–4 days.

Biochemical Measurements

As described above, tissue culture cells were grown in the presence or absence of test compounds, collected from tissue culture flasks using trypsin, washed twice with PBS and subjected to biochemical analysis. VLCFA measurements was conducted by extracting total amount of lipids, converted the lipids to methyl ester, purified by TLC, and subjected to capillary CC analysis as described in Moser et al., *Technique in Diagnostic Biochemical Genetics: A Laboratory Manual* (ed. A., H F.) 177–191 (Wiley-Liss, New York, 1991). Duplicate assays were set up independently and were assayed on different days. C24:0 β-oxidation activity of lymphoblastoid cells was determined by measuring their capacity to degrade [1-$^{14}$C]-C24:0 fatty acid to water-soluble products as described in Watkins et al., *Arch. Biochem. Biophys.* 289, 329–336 (1991). The statistical significance of measured biochemical differences between untreated and treated X-ALD cells can be determined by a two-tailed Student's t-test.

Compounds of the invention were found to decrease the cellular content of the VLCFA by approximately 60 percent in the X-ALD cells.

EXAMPLE 32

Cystic Fibrosis Screening Assay

As described above, during its biosynthesis, CFTR is initially synthesized as a nascent polypeptide chain in the rough ER, with a molecular weight of around 120 kDa (Band A). It rapidly receives a core glycosylation in the ER, giving it a molecular weight of around 140 kDa (Band B). As CFTR exits the ER and matures through the Golgi stacks, its glycosylation is modified until it achieves a terminal mature glycosylation, affording it a molecular weight of around 170 kDa (Band C). The extent to which CFTR exits the ER and traverses the Golgi to reach the plasma membrane may be reflected in the ratio of Band B to Band C protein. CFTR is immunoprecipitated from control cells, and cells exposed to test compounds. Both wt CFTR and ΔF508 CFTR expressing cells are tested. Following lysis, CFTR are immunoprecipitated using various CFTR antibodies. Immunoprecipitates are then subjected to in vitro phosphorylation using radioactive ATP and exogenous protein kinase A. Samples are subsequently solubilized and resolved by SDS-PAGE. Gels are then dried and subject to autoradiography and phosphor image analysis for quantitation of Bands B and C are determined on a BioRad personal fix image station.

Cell Culture

Chinese hamster ovary (CHO) cells stably expressing both wt and ΔF508 CFTR were used in these assays. The cultures were grown on 100 mm plastic cell dishes in DMEM containing 10% foetal bovine serum (FBS) and kept at 5% $CO_2$/95% $O_2$ at 37° C. Cells were grown to confluence and used 3–5 days post-plating. All test compounds were added to cells for 24 hours prior to analysis.

Immunoprecipitation

Cells were treated with test compounds and CFTR immunoprecipitated as described in Bradbury et al., *Am. J. Physiol.* 276, L659–668 (1999). Briefly, treated cells were lysed in buffer containing 1% TRITON X-100 and various protease inhibitors. Soluble material was immunoprecipitated using both R domain and C-terminal monoclonal antibodies. Immunoprecipitated CFTR was then subject to in vitro phosphorylation using camp-dependent PKA catalytic subunit and [γ-32P]ATP, followed by resolution on SDS-PAGE gels. After fixation, the gels were dried and processed for autoradiography and phosphor image analysis. Quantitation of B and C bands on a BioRad personal fix image analysis station.

It was found that compounds of the invention (at 100 μM) showed no significant changes in the levels of Bands B and C in treated cells relative to untreated cells. Based on the results obtained from using these test compounds, there was no gross effect of the test compounds on the expression levels of wild type CFTR. Analysis of band C of ΔF508 CFTR CHO cells showed that very little Band C was present in ΔF508 cells compared to wild-type cells. Exposure of these cells to test compounds at 100 μM for 24 hours at 37° C. did not affect the level of Band C CFTR in either wild-type or ΔF508 CFTR expressing cells. In contrast, analysis of Band B CFTR in ΔF508 cells showed that test compounds at 100 μM resulted in a significant increase (about 6–7 fold) in the level of Band B compared to ΔF508 cells not exposed to the test compounds.

EXAMPLE 33

Toxicity Assay

Test compounds of the invention were administered to three groups of 10 mice at 100, 300, and 1,000 mg/kg. An additional group received vehicle (20% hydroxypropyl-β-cyclodextrin aqueous solution) at 10 mL/kg. Mortality/morbidity checks were made twice daily. Clinical observations were recorded predose and/or postdose on Day 1, and daily thereafter through Day 8. Body weights were recorded on the day of dosing (Day 1) and on Day 8. Mice were euthanized by $CO_2$ asphyxiation and necropsied on Day 8 or upon death.

One test compound was tested so far and based on the results obtained, the no-observed toxicity level for this compound when administered to CD-1 mice as a single intraperitoneal does 100 mg/kg. Clinical signs of toxicity were noted after dosing at 300 mg/kg with recovery within 24 hours, while dosing at 1,000 mg/kg resulted in death (80% of animals) by the end of Day 2.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of inhibiting histone deacetylation activity in cells comprising contacting the cells with an effective amount of a compound wherein the compound is 7-phenyl-2,4,6-hepta-trienoylhydroxamic acid, 8-phenyl-3,5,7-octatrienoic acid, cinnamoylhydroxamic acid, methyl-cinnamoylhydroxamic acid, 5-phenyl-2,4-pentadienoylhydroxamic acid, N-methyl-5-phenyl-2,4-pentadienoylhydroxamic acid, 3-methyl-5-phenyl-2,4-pentadienoylhydroxamic acid, 4-methyl-5-phenyl-2,4-pentadienoyl hydroxamic acid, 5-phenyl-2-en-4-yn-pentanoylhydroxamic acid, or N-methyl-6-phenyl-3,5-hexadienoylhydroxamic acid, thereby treating one or more disorders mediated by histone deacetylase; wherein the disorder is cancer;

and determining whether the level of acetylated histones in the treated cells is higher than in untreated cells under the same conditions.

2. The method of claim 1, wherein said compound 7-phenyl-2,4,6-hepta-trienoylhydroxamic acid.

3. The method of claim 1, wherein the cells being treated are cancerous.

4. The method of claim 1, wherein said compound is cinnamoylhydroxamic acid.

5. The method of claim 1, wherein said compound is methyl-cinnamoylhydroxamic acid.

6. The method of claim 1, wherein said compound is 5-phenyl-2,4-pentadienoylhydroxamic acid.

7. The method of claim 1, wherein said compound is N-methyl-5-phenyl-2,4-pentadienoylhydroxamic acid.

8. The method of claim 1, wherein said compound is 3-methyl-5-phenyl-2,4-pentadienoylhydroxamic acid.

9. The method of claim 1, wherein said compound is 4-methyl-5-phenyl-2,4-pentadienoyl hydroxamic acid.

10. The method of claim 1, wherein said compound is 5-phenyl-2-en-4-yn-pentanoylhydroxamic acid.

11. The method of claim 1, wherein said compound is N-methyl-6-phenyl-3,5-hexadienoylhydroxamic acid.

\* \* \* \* \*